US012693519B2

(12) United States Patent
Schultheis et al.

(10) Patent No.: US 12,693,519 B2
(45) Date of Patent: Jul. 28, 2026

(54) MULTI-COMPONENT ENDOSCOPE AND DISPOSABLE ENDOSCOPE SYSTEM

(71) Applicants:SCHOTT AG, Mainz (DE); SCHOTT CORPORATION, Rye Brook, NY (US)

(72) Inventors: Bernd Schultheis, Schwabenheim (DE); Martin Cramer, Wiesbaden (DE); Hubertus Russert, Jugenheim (DE); Holger Werner, Frankfurt (DE); Jürgen Meinl, Hohenstein-Holzhausen (DE); Jonas Grimm, Bad Schwalbach (DE); Oliver Keiper, Hünstetten (DE); Steffen Astheimer, Hünstetten (DE); Björn Bleisinger, Riesweiler (DE); Christian Schwedler, Mainz (DE)

(73) Assignees: SCHOTT AG, Mainz (DE); SCHOTT CORPORATION, Rye Brook, NY (US)

( * ) Notice: Subject to any disclaimer, the term of this patent is extended or adjusted under 35 U.S.C. 154(b) by 0 days.

(21) Appl. No.: 17/202,235

(22) Filed: Mar. 15, 2021

(65) Prior Publication Data

US 2021/0282631 A1 Sep. 16, 2021

(30) Foreign Application Priority Data

Mar. 13, 2020 (DE) .................... 10 2020 106 915.4

(51) Int. Cl.
*G02B 23/24* (2006.01)
*A61B 1/00* (2006.01)
(Continued)

(52) U.S. Cl.
CPC ...... *G02B 23/2469* (2013.01); *A61B 1/00009* (2013.01); *A61B 1/00103* (2013.01);
(Continued)

(58) Field of Classification Search
CPC ..... A61B 1/07; A61B 1/00103; A61B 1/0011; A61B 1/05; A61B 1/0669; A61B 1/0684;
(Continued)

(56) References Cited

U.S. PATENT DOCUMENTS 3,581,738 A 6/1971 Moore
4,141,710 A * 2/1979 Aulich .................. C03C 25/106
65/60.8
(Continued)

FOREIGN PATENT DOCUMENTS

CN 103906548 7/2014
CN 110268300 A 9/2019
(Continued)

OTHER PUBLICATIONS

EN 60601-1, 3rd edition, table 3, 2005.
(Continued)

*Primary Examiner* — John P Leubecker
(74) *Attorney, Agent, or Firm* — Ruggiero McAllister & McMahon LLC

(57) ABSTRACT

An endoscope is provided that has a first component having an LED that emits light and a second component having a proximal end, a distal end, an image capturing element, and a light guide. The proximal end is coupled to the first component. The image capturing element being arranged at the distal end. The light guide comprising an optical fiber extending through the second component. The LED is coupled to the proximal end such that the light is injected into the optical fiber and is conducted from the LED at the proximal end to the distal end and to emit the light at the distal end. The optical fiber has a cross section of at least 80 μm and has a polymer-based coating or a protective sheathing made of a polymer-based tube material arranged on an outer surface.

29 Claims, 3 Drawing Sheets

(51) Int. Cl.
    *A61B 1/05*         (2006.01)
    *A61B 1/06*         (2006.01)
    *A61B 1/07*         (2006.01)
    *A61M 25/00*      (2006.01)

(52) U.S. Cl.
    CPC .............. *A61B 1/0011* (2013.01); *A61B 1/05*
        (2013.01); *A61B 1/0669* (2013.01); *A61B*
        *1/0684* (2013.01); *A61B 1/07* (2013.01);
        *A61M 25/0045* (2013.01)

(58) Field of Classification Search
    CPC . A61B 1/00009; A61B 1/0002; A61B 1/3137;
        A61B 1/053; A61B 1/04; A61M 25/0045;
        G02B 23/2484; G02B 23/2469
    See application file for complete search history.

(56)           References Cited

U.S. PATENT DOCUMENTS

| | | | | |
|---|---|---|---|---|
| 4,264,131 A * | 4/1981 | Sawamura | ............... | G02B 6/02 |
| | | | | 501/67 |
| 4,362,542 A * | 12/1982 | Macedo | ............ | C03B 37/01807 |
| | | | | 65/429 |
| 4,783,135 A | 11/1988 | Utsumi | | |
| 4,807,597 A | 2/1989 | Tsuno | | |
| 4,867,529 A | 9/1989 | Utsumi | | |
| 4,964,710 A | 10/1990 | Leiner | | |
| 5,188,094 A * | 2/1993 | Adair | ....................... | A61B 1/05 |
| | | | | 600/122 |
| 5,363,135 A * | 11/1994 | Inglese | ................ | A61B 1/0607 |
| | | | | 348/66 |
| 5,436,655 A | 7/1995 | Hiyama | | |
| 5,615,293 A * | 3/1997 | Sayegh | ................ | G02B 6/4403 |
| | | | | 385/100 |
| 5,704,892 A * | 1/1998 | Adair | .................... | A61B 1/015 |
| | | | | 600/125 |
| 5,704,899 A * | 1/1998 | Milo | ........................ | B29C 48/05 |
| | | | | 600/161 |
| 5,761,356 A | 6/1998 | Li | | |
| 5,864,644 A * | 1/1999 | DiGiovanni | ......... | G02B 6/2856 |
| | | | | 385/48 |
| 6,249,348 B1 | 6/2001 | Jung | | |
| 6,252,722 B1 | 6/2001 | Kittaka | | |
| 6,260,994 B1 * | 7/2001 | Matsumoto | .......... | A61B 1/0684 |
| | | | | 362/574 |
| 6,293,910 B1 | 9/2001 | Yamakita | | |
| 6,398,721 B1 | 6/2002 | Nakamura | | |
| 6,556,851 B1 | 4/2003 | Ott | | |
| 8,329,602 B2 * | 12/2012 | Ogino | .................... | C03C 3/064 |
| | | | | 501/72 |
| 8,409,082 B2 * | 4/2013 | Irion | .................. | A61B 1/00124 |
| | | | | 362/572 |
| 10,393,957 B1 | 8/2019 | Potter | | |
| 11,215,752 B1 | 1/2022 | Lin | | |
| 2003/0042493 A1 | 3/2003 | Kazakevich | | |
| 2004/0086245 A1 * | 5/2004 | Farroni | .................. | G02B 6/024 |
| | | | | 385/142 |
| 2004/0240815 A1 * | 12/2004 | Kuksenkov | ......... | C03B 37/0146 |
| | | | | 385/123 |
| 2004/0246744 A1 | 12/2004 | Krupa | | |
| 2005/0197623 A1 * | 9/2005 | Leeflang | .............. | A61B 1/0055 |
| | | | | 604/95.04 |
| 2005/0226580 A1 * | 10/2005 | Samson | ................ | G02B 6/105 |
| | | | | 385/127 |
| 2005/0283048 A1 | 12/2005 | Gill | | |
| 2006/0041193 A1 | 2/2006 | Wright | | |
| 2006/0069314 A1 | 3/2006 | Farr | | |
| 2006/0072893 A1 | 4/2006 | Wied | | |
| 2006/0152926 A1 | 7/2006 | Hama | | |
| 2006/0173245 A1 * | 8/2006 | Todd | .................... | A61B 1/0653 |
| | | | | 600/178 |
| 2006/0279950 A1 | 12/2006 | Hama | | |
| 2007/0249907 A1 * | 10/2007 | Boulais | ................ | A61B 1/0676 |
| | | | | 600/179 |

| | | | | |
|---|---|---|---|---|
| 2008/0013900 A1 | 1/2008 | Harris | | |
| 2008/0142828 A1 * | 6/2008 | Yang | .................... | G02B 6/4246 |
| | | | | 257/E31.022 |
| 2008/0188910 A1 * | 8/2008 | Spaide | ................ | A61F 9/00821 |
| | | | | 606/15 |
| 2008/0232131 A1 * | 9/2008 | Suda | .................... | A61B 1/0655 |
| | | | | 362/574 |
| 2008/0300456 A1 | 12/2008 | Irion | | |
| 2009/0163342 A1 | 6/2009 | Kolberg | | |
| 2009/0312607 A1 | 12/2009 | Sunagawa | | |
| 2009/0321348 A1 | 12/2009 | Hoermann | | |
| 2010/0010314 A1 | 1/2010 | Krattiger | | |
| 2010/0046897 A1 | 2/2010 | Toriya | | |
| 2010/0210911 A1 * | 8/2010 | Shimotsu | ................. | A61B 1/07 |
| | | | | 600/178 |
| 2011/0182552 A1 | 7/2011 | Russert | | |
| 2011/0275894 A1 * | 11/2011 | Mackin | .............. | A61B 1/00016 |
| | | | | 600/109 |
| 2011/0282160 A1 | 11/2011 | Bhadri | | |
| 2012/0010465 A1 | 1/2012 | Erikawa | | |
| 2012/0174931 A1 | 7/2012 | Nilsson | | |
| 2012/0190990 A1 * | 7/2012 | Ohzawa | ................. | G02B 23/26 |
| | | | | 600/478 |
| 2012/0289779 A1 | 11/2012 | Kinoshita | | |
| 2012/0296165 A1 * | 11/2012 | Segawa | ................ | A61B 1/0011 |
| | | | | 600/109 |
| 2013/0060087 A1 * | 3/2013 | Yoshida | ................... | A61B 1/07 |
| | | | | 600/112 |
| 2013/0172673 A1 * | 7/2013 | Kennedy | .............. | A61B 1/2736 |
| | | | | 600/109 |
| 2013/0175720 A1 * | 7/2013 | Otsuka | .................... | B29C 45/16 |
| | | | | 264/1.32 |
| 2013/0193875 A1 * | 8/2013 | Godo | ...................... | A61B 1/044 |
| | | | | 315/297 |
| 2013/0342110 A1 | 12/2013 | Yamamoto | | |
| 2014/0107630 A1 * | 4/2014 | Yeik | ........................ | A61F 9/008 |
| | | | | 606/5 |
| 2014/0221749 A1 | 8/2014 | Grant | | |
| 2014/0288371 A1 * | 9/2014 | Nakatate | ................ | A61B 1/015 |
| | | | | 600/156 |
| 2014/0303551 A1 | 10/2014 | Germain | | |
| 2014/0350343 A1 | 11/2014 | Kim | | |
| 2014/0376868 A1 | 12/2014 | Ritter | | |
| 2015/0016140 A1 | 1/2015 | Weingärtner | | |
| 2015/0049994 A1 | 2/2015 | Schultheis | | |
| 2015/0099929 A1 * | 4/2015 | Blumenzweig | ........ | A61B 1/045 |
| | | | | 600/110 |
| 2015/0216418 A1 | 8/2015 | Ammon | | |
| 2015/0305602 A1 | 10/2015 | Gal | | |
| 2015/0305603 A1 * | 10/2015 | Gal | ...................... | A61B 1/0669 |
| | | | | 600/109 |
| 2015/0374217 A1 | 12/2015 | Sinofsky | | |
| 2016/0022119 A1 | 1/2016 | Shahmoon | | |
| 2016/0227985 A1 * | 8/2016 | Ikeda | ...................... | A61B 1/008 |
| 2016/0262597 A1 * | 9/2016 | Danchinyu | ............ | A61B 1/042 |
| 2016/0334616 A1 | 11/2016 | Vayser | | |
| 2017/0003164 A1 | 1/2017 | Tanaka | | |
| 2017/0007107 A1 * | 1/2017 | Scheller | .................... | A61B 1/07 |
| 2017/0042573 A1 * | 2/2017 | Savvouras | ......... | A61B 17/3474 |
| 2017/0052319 A1 | 2/2017 | Schultheis | | |
| 2017/0100024 A1 * | 4/2017 | Shahmoon | ......... | G02B 6/02042 |
| 2017/0215715 A1 * | 8/2017 | Harrah | .................... | A61B 1/307 |
| 2017/0231477 A1 | 8/2017 | Del Nido | | |
| 2017/0231698 A1 | 8/2017 | Goldfarb | | |
| 2017/0276891 A1 | 9/2017 | Esseghir | | |
| 2017/0307872 A1 * | 10/2017 | Hatase | ................. | A61B 1/0684 |
| 2018/0055342 A1 | 3/2018 | Sakai | | |
| 2018/0078127 A1 * | 3/2018 | Igarashi | ................ | G02B 23/26 |
| 2018/0228354 A1 | 8/2018 | Yabe | | |
| 2019/0014979 A1 | 1/2019 | Czupalla | | |
| 2019/0038120 A1 | 2/2019 | Maclean | | |
| 2019/0086657 A1 * | 3/2019 | Sueyoshi | ............... | A61B 1/051 |
| 2019/0270667 A1 * | 9/2019 | Sumita | .................... | G02B 6/02 |
| 2019/0290100 A1 | 9/2019 | Ramachandran | | |
| 2019/0346649 A1 * | 11/2019 | Tanaka | ................. | A61B 1/0017 |
| 2019/0374095 A1 * | 12/2019 | Lord | ...................... | A61B 1/053 |
| 2020/0077880 A1 * | 3/2020 | Ouyang | .............. | A61B 1/0057 |
| 2020/0178781 A1 | 6/2020 | Tabata | | |

(56) References Cited

U.S. PATENT DOCUMENTS

| | | | |
|---|---|---|---|
| 2020/0222712 | A1 | 7/2020 | Schultheis |
| 2020/0253592 | A1* | 8/2020 | Popejoy ............. A61B 17/0206 |
| 2020/0301064 | A1* | 9/2020 | Kojima ................... A61B 5/42 |
| 2021/0022588 | A1 | 1/2021 | Schultheis |
| 2021/0093170 | A1 | 4/2021 | Schultheis |
| 2021/0093174 | A1* | 4/2021 | Kim ................... A61B 1/00096 |
| 2021/0145257 | A1* | 5/2021 | Levinson .......... A61B 1/00066 |
| 2021/0267439 | A1* | 9/2021 | Onobori ................... A61B 1/05 |
| 2021/0282631 | A1 | 9/2021 | Schultheis |
| 2022/0175226 | A1* | 6/2022 | Sørensen ................ A61B 1/07 |

FOREIGN PATENT DOCUMENTS

| | | |
|---|---|---|
| DE | 1596485 | 7/1970 |
| DE | 3724749 | 2/1988 |
| DE | 69720736 | 3/2004 |
| DE | 102004048741 | 5/2006 |
| DE | 102006053487 | 5/2008 |
| DE | 102006040214 | 7/2008 |
| DE | 102007026234 | 12/2008 |
| DE | 102008044938 | 3/2010 |
| DE | 102009004159 | 7/2010 |
| DE | 102011114575 | 4/2013 |
| DE | 102012100233 | 5/2014 |
| DE | 102013208838 | 3/2015 |
| DE | 102011119972 | 10/2015 |
| DE | 102014208756 | 11/2015 |
| DE | 102015015041 | 5/2017 |
| DE | 102017108698 | 10/2018 |
| DE | 102017122756 | 4/2019 |
| DE | 102018107523 | 10/2019 |
| DE | 102019125912 | 4/2021 |
| EP | 1890173 | 2/2008 |
| EP | 2072477 | 3/2010 |
| EP | 3097845 | 11/2016 |
| GB | 1242883 | 8/1971 |
| JP | S55150400 | 11/1980 |
| JP | S61143120 | 9/1986 |
| JP | S61264305 | 11/1986 |
| JP | S63151918 | 6/1988 |
| JP | H01302207 | 12/1989 |
| JP | H073489 A | 1/1995 |
| JP | H0713087 A | 1/1995 |
| JP | H07327923 A | 12/1995 |
| JP | H09269426 | 10/1997 |
| JP | H10258022 | 9/1998 |
| JP | 2000079089 | 3/2000 |
| JP | 2000316798 | 11/2000 |
| JP | 2001117021 | 4/2001 |
| JP | 2002531846 | 9/2002 |
| JP | 2003290135 | 10/2003 |
| JP | 2005283765 | 10/2005 |
| JP | 2005294288 | 10/2005 |
| JP | 2006091722 | 4/2006 |
| JP | 2006317537 | 11/2006 |
| JP | 2007148418 | 6/2007 |
| JP | 2007260192 | 10/2007 |
| JP | 2008532641 | 8/2008 |
| JP | 2008544809 | 12/2008 |
| JP | 2009018081 | 1/2009 |
| JP | 2009268635 | 11/2009 |
| JP | 2011033958 | 2/2011 |
| JP | 2012120764 | 6/2012 |
| JP | 2012254193 | 12/2012 |
| JP | 2013165749 | 8/2013 |
| JP | 2014066923 | 4/2014 |
| JP | 2015228887 | 12/2015 |
| JP | 2016034505 | 3/2016 |
| JP | 2016052533 | 4/2016 |
| JP | 2016093533 | 5/2016 |
| JP | 2016201200 | 12/2016 |
| JP | 2017524505 | 8/2017 |
| JP | 2017195960 | 11/2017 |
| JP | 2017211472 | 11/2017 |
| JP | 2018015250 | 2/2018 |
| JP | 2018504629 | 2/2018 |
| KR | 20080028893 | 4/2008 |
| WO | 8912479 | 12/1989 |
| WO | 9835607 | 8/1998 |
| WO | 98035607 | 8/1998 |
| WO | 2013092498 | 6/2013 |
| WO | 2016185537 | 11/2016 |
| WO | 2017043170 | 3/2017 |
| WO | 2018116302 A1 | 6/2018 |
| WO | 2019185645 | 10/2019 |

OTHER PUBLICATIONS

European Medical Device Directive MDD 93/42 EEC, Jun. 1993.
Regulation (EU) 2017/745 of Apr. 5, 2017.
DIN EN ISO 10993, Fifth Edition, Aug. 2018.
English translation of DIN EN ISO 10993-1: Apr. 2010.
Hewak, "Fiber and guided wave optics—Fabrication of Optical Fiber", Encyclopedia of Modern Optics 2005, Abstract.
DIN EN ISO 10993-5, "Biological evaluation of medical devices—Part 5: Tests for in vitro cytotoxicity (ISO 10993-5:2009) English version of DIN EN ISO 10993-5:2009-10", Oct. 2009, 44 pages.
"Synthetic Polymer Materials", Beijing Institute of Technology Press, 2019, pp. 220-224, with English machine translation.
3M Science Applied to Life—Categorizing Surface Energy (https://www.3m.com/3M/en_US/bonding-and-assembly-us/resources/science-of-adhesion/categorizing-surface-energy/) 3M. (Year: 2025).

* cited by examiner

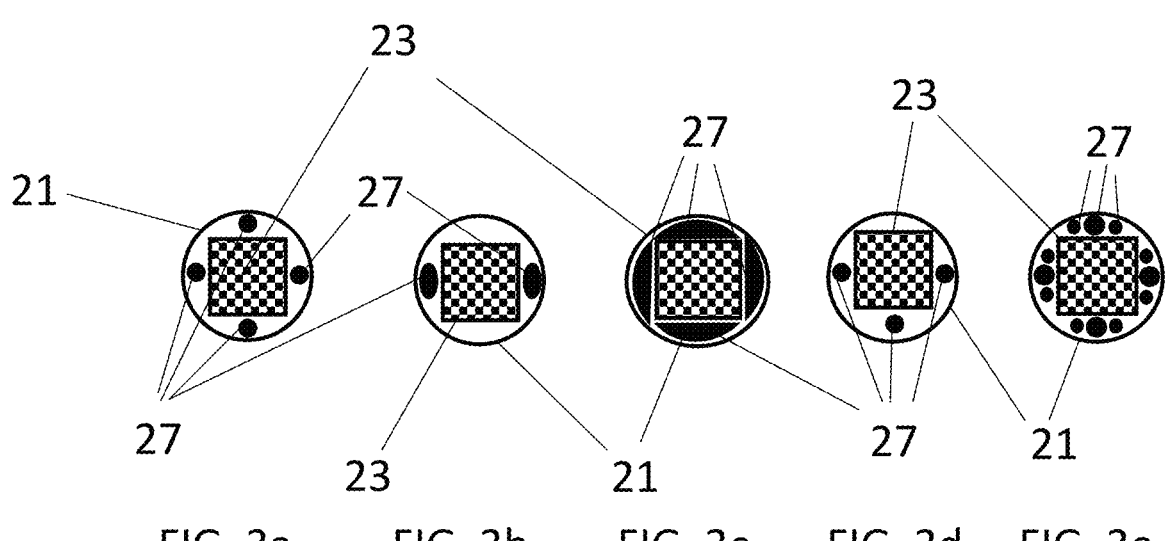
FIG. 3a    FIG. 3b    FIG. 3c    FIG. 3d    FIG. 3e
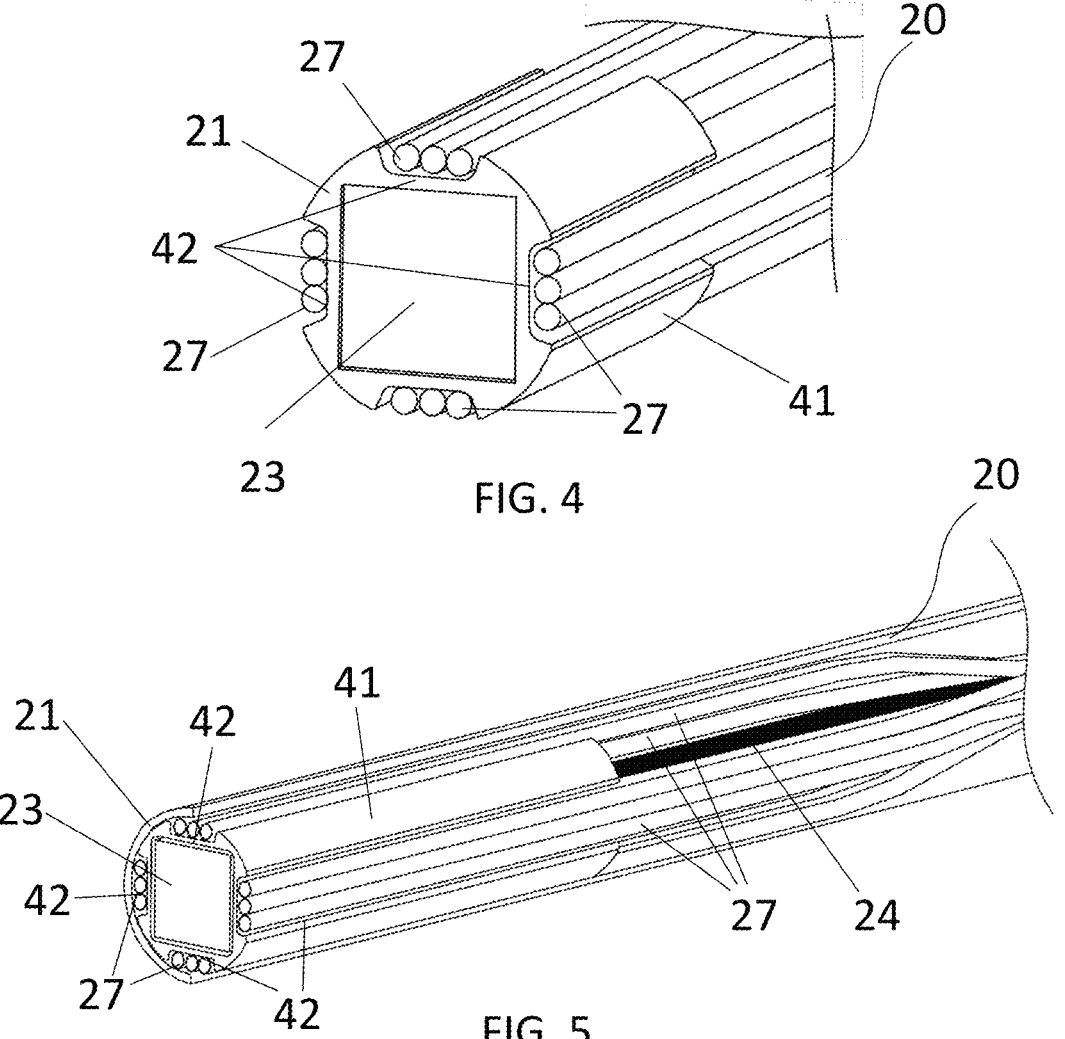
FIG. 4
FIG. 5

MULTI-COMPONENT ENDOSCOPE AND DISPOSABLE ENDOSCOPE SYSTEM

CROSS REFERENCE TO RELATED APPLICATIONS

This application claims benefit under 35 USC § 119 of German Application 10 2020 106 915.4 filed Mar. 13, 2020, the entire contents of which are incorporated herein by reference.

BACKGROUND

1. Field of the Invention

The invention generally relates to endoscopes and endoscope systems, more particularly to disposable endoscopes and/or disposable endoscope systems.

2. Description of Related Art

Diagnostic, surgical, and/or therapeutic devices such as endoscopes for diagnosis, for minimally invasive interventions, or for therapy are known to have rigid or flexible designs and have been sufficiently described in the literature. Nowadays, disposable endoscope are increasingly being used, in particular to increase patient safety during medical examinations, therapies and/or minimally invasive interventions, since single use allows to prevent contamination. In fact, prior art endoscopes have been designed so as to be reprocessable in terms of medical technology, i.e. they can be cleaned, sterilized and, above all, they are autoclavable.

Nevertheless, it may occasionally happen, due to incorrect application of reprocessing or unfavorable design of such devices, that the necessary reduction in the number of bacteria fails to be achieved and hence bacteria may be transferred to the patient during the next application. This can be prevented by using such disposable endoscopes.

Another aspect for the increased use of disposable endoscopes is economic assessment. In particular the reprocessing process that has to be carried out properly and regularly after each treatment implies high costs for the practicing doctor or the clinic nowadays. Moreover, high investments are required for purifying devices such as thermal disinfectors and autoclave devices and/or plasma sterilization devices, so that, overall, the use of such disposable endoscopes is justified.

Another advantage results from the fact that such disposable endoscopes can be used as transportable hand-held devices and can therefore also be employed in emergency medicine, in military emergency missions or in regions that are difficult to access, for example during disaster relief missions, where in particular reprocessing options are not available.

Such disposable endoscopes, also known as single-use endoscopes, as described in the literature have been described in the following documents, for example:

Document U.S. Pat. No. 3,581,738 A1 discloses a disposable endoscope comprising a body of synthetic resinous material having a generally tubular side wall defining a speculum and a unitary elongated light-conducting member embedded in the side wall, the member being formed of a light-conducting material clad with a transparent material having an index of refraction different from that of the light-conducting material, the body being formed of two mating halves divided axially of the endoscope, each half having a member-enclosing wall.

Document U.S. Pat. No. 4,964,710 A1 describes a rigid endoscope equipped with an objective lens system, an ocular lens and an intermediate relay lens. The relay system is a hybrid system that uses both plastic and glass components. The plastic components comprise an even number (N) of axially aligned lenses, each having a length which is of the order of their diameter. The glass components comprise an odd number (N minus 1) of axially aligned plano glass cylinders with polished end faces.

Document EP 1890173 A1 discloses a method for producing an optical light guide that can be used in such endoscopes. A plurality of optical fibers are bundled, and the fiber bundle is cut at a part of a mouthpiece which is fixed to an intermediate part of the fiber bundle. Thus, the fiber bundle is divided into a first optical fiber bundle and a second optical fiber bundle. Separation surfaces of the first and second optical fiber bundles have the same properties and condition since the first and second optical fiber bundles are formed of the fiber bundle that is obtained by bundling the same optical fibers. The first optical fiber bundle is assembled in an insertion section of an endoscope and the second optical fiber bundle is assembled in a flexible tube, whereby a first light guide is formed in the insertion section of the endoscope and a second light guide is formed in the flexible tube. Thereby, a separable light transmission path of the light guide is formed.

Since such endoscopes are subject to high cost pressure due to their single use, the assemblies and components have to be producible in a cost-effective way. Among the main components for imaging and illumination are light guides or image guides, and these are currently still assembled and processed in rather complex processing steps. What makes the current light guides or image guides comparatively expensive is often due to complex mechanical components partly combined with optical elements such as lenses that form part of such light guides or image guides, and sometimes complex processing steps such as grinding and polishing of the end faces are moreover involved.

On the other hand, particular lighting requirements must also be taken into account when using endoscopes, especially in medical technology. In addition to transmitting the light provided by a light source to the examination site in the best possible loss-free manner, this includes a true-to-color or an intentionally colored representation of the examination site and also the avoiding of introducing unnecessary heat to the examination site. A particular challenge lies in the luminous flux provided by the light source as well as the transmission of the light to the distal end of an endoscope. Especially endoscope systems with a small diameter require extremely bright light sources on the one hand and luminous flux-optimized light guides on the other.

If active electronic components are used, such as camera chips and/or LEDs for lighting, it is moreover necessary to take into account requirements with regard to electrical insulation, electrical shielding and patient leakage currents, which must not exceed maximum threshold values, depending on the field of application of the endoscope. For applications at the heart, for example, a maximum leakage current of 10 µA is required, corresponding to CF classification (see EN 60601-1, $3^{rd}$ edition, tab. 3).

Further requirements, for example with respect to shielding in particular a camera chip from scattered light of light guides that may deteriorate image quality and/or give rise to image artefacts, may also arise.

In addition to these illumination-related and electrical requirements, requirements regarding biocompatibility must also be observed. For biocompatibility it is necessary to ensure that the material is compatible with the human organism. For medical devices that might come into contact with the human body, regulatory requirements request to determine and assess possible interactions and undesirable side effects. The selection of the required tests depends on the type of contact and duration of contact in the human body. According to European Medical Device Directive MDD 93/42 EEC (MDD for short) and Regulation (EU) 2017/745 of Apr. 5, 2017 (MDR for short), this biological assessment of a product is always necessary if there is direct contact between the material or product and the patient.

The main standards for biological tests and evaluation of materials are DIN EN ISO 10993 and the test according to United States Pharmacopeia Class VI (USP Class VI). Although the much more extensive ISO 10993 was originally intended to replace the test according to USP Class VI, the USP test is used very frequently today in particular for evaluating biocompatible plastics. For this purpose, the materials intended for invasive application are evaluated with regard to their chemical compounds on the one hand, and are on the other hand subjected to a cytotoxicity test in which possible toxic effects to living cell cultures are examined. The requirements for this are summarized in DIN EN ISO 10993, especially in parts −1 and −5 (DIN EN ISO 10993-1: 2010-04). In the United States, this is subject to FDA requirements. The requirements corresponding to DIN EN ISO 10993 are specified in USP Class VI there.

Another advantage of the endoscopes in the form of single-use endoscopes is that they do not require to take into account the known reprocessing methods in the form of cleaning or disinfection processes involving strongly basic solutions and sterilization by autoclaving at temperatures of up to 135° C. and typical steam pressures of about 3 bar, which in particular permits to choose more cost-effective materials. The only thing that needs to be considered for the materials is their suitability for gas sterilization processes, such as ethylene oxide sterilization, and the RoHS (Restriction of Hazardous Substances) and REACH (Registration, Evaluation, Authorisation and Restriction of Chemicals) regulations.

The Applicant's own applications DE 10 2019 125 912 and DE 10 2018 107 523 relate to various aspects of light guides. A laser-based light source is not mentioned.

U.S. Pat. No. 6,398,721 B relates to a surgical microscopy device which may comprise a laser diode.

U.S. patent application US 2006/0279950 A1 discloses an LED. Endoscopes are not mentioned, but light guides comprising fibers can be used, for example.

U.S. patent application US 2006/0152926 A1 also describes an LED which may also be used in endoscopes byway of example. The LED is operated in transmission.

A highly efficient light source is described in U.S. patent application US 2004/0246744 A1.

U.S. patent application US 2019/0290100 A1 describes an optical imaging system which can be used in particular in fluorescence microscopy (STED microscopy).

U.S. patent application US 2006/0069314 A1 describes a solid-state light source for an endoscope.

German patent application DE 10 2017 108 698 A1 discloses an optoelectronic component.

With respect to endoscope systems, in particular regarding single-use endoscopes, having small cross sections, for example an overall cross section of at most 3 mm or less, the high assembly effort required for conventional fiber bundles comprising several hundred single fibers has proven disadvantageous. Further, for such fiber bundles less space is available, so that the light output at the distal end of such an endoscopes is a further challenge.

SUMMARY

The object of the invention is to at least partially overcome or at least mitigate the deficiencies of the prior art, and in particular to provide endoscope systems which comprise a bright light source or lighting with sufficiently high brightness in particular for single-use applications, and an light guiding system optimized for this purpose, which further is easy to assemble.

The invention therefore relates to an endoscope comprising a first component and a second component, with the second component having a proximal end that is coupled to the first component, preferably a detachably coupled proximal end, and a distal end. An element for image capturing such as a camera chip or a fiber optic element is arranged at the distal end. A light guide comprising at least one optical fiber extends through the second component to conduct light of the light source from the proximal end to the distal end and to emit it at the distal end; and preferably a power supply line for electrically powering the camera chip.

The first component may comprise a light source integrated therein, wherein the light source comprises at least one LED-chip for emitting light, and wherein the LED-chip is coupled to the proximal end of the second component coupled to the first component such that the light emitted by the LED-chip may be injected into the light guide.

It is, however, also possible that the light source is formed as an integrated component of a plug-in connector. In that case, the plug-in connector is formed as the proximal end of the second component comprising its light guide. Here, the light source comprises at least one integrated LED, preferably an integrally mounted LED, whose emitted light may be injected into the at least one optical fiber of the light guide.

In each case, the at least one optical fiber has a cross section of at least 80 µm, wherein the at least one optical fiber has a polymer-based coating or a protective sheathing made of a polymer-based tube material arranged on its outer surface, at least on parts or sections thereof.

The coating and/or the protective sheathing are as a rule arranged continuously on the outer fiber surface, that is, fully covering the outer fiber surface. It may, however, also be contemplated to arrange the coating and/or the protective sheathing only in parts or sections of the outer surface, for example in those parts or sections with high mechanical load. It is further also possible that the coating and/or that the protective sheathing are first applied over or arranged on the whole outer surface, but that the coating and/or the sheathing are subsequently removed in parts or sections of the outer surface of the at least one optical fiber. This may be advantageous and/or necessary for those parts used for mounting or gluing, for example at the distal end, that is, directed towards a camera chip.

Fiber optic elements for image capturing or image transfer are also known as "image guides" and consist of some tens of thousands of individual fibers arranged in a mutually ordered manner on the end faces. Such fiber-optic elements may in particular be made of glass or of plastics or may comprise glass or plastics, for example in the form of glass optical fibers or plastic optical fibers.

Such a configuration of an endoscope has a number of advantages.

According to the present disclosure, the endoscope is divided into two components. The first component which may also be referred to as the proximal component may, for example, have a light source integrated therein, which comprises at least one LED-chip adapted to emit light, wherein the LED-chip is coupled with the proximal end of the second component joined to the first component that the light emitted by the LED chip may be injected into the at least one optical fiber of the light guide.

According to a variant of the endoscope it may be provided for the light source to be an integrated component of a plug-in connector, that is, mounted within the plug-in connector, preferably integrally mounted, the plug-in connector being formed as the proximal end of the second component comprising its light guide. In that case, the light source comprises at least one integrated, preferably integrally mounted, LED, that injects emitted light into the at least one optical fiber of the light guide. Such an approach has also been described in patent document DE 10 2011 119 972 B4 of the applicant, the latter document primarily targeting low cost fiber optic lighting facilities.

In other words, the first component is according to both variants described above in each case designed so as to be connectable to a second component which may also be referred to as a distal component, or it may even be provided in a form connected to the second component.

Depending on the precise configuration and the type of associated elements, the first component may be provided in the form of a handpiece, for example, that is to say as a component that also serves to manipulate and/or hold the endoscope, for example. However, it is also possible that the first component comprises elements which serve to control and/or operate an endoscope, for example in the form of a control and/or evaluation unit, so that in this case the first component may also be configured as an operating device for the endoscope.

Furthermore, the endoscope comprises a second component, which has a proximal end and a distal end and a light guide comprising at least one optical fiber extending through the second component. The light guide is adapted to conduct light of the light source from the proximal end to the distal end and to emit it at the distal end. An image capturing element such as a camera chip for image capturing or a fiber optic image guide is arranged at the distal end. Furthermore, if the distal end comprises a camera chip, the second component preferably comprises a power supply line for electrically powering the camera chip.

Such a configuration of the endoscope with two components (or assemblies) is advantageous. This is because according to the described implementation the endoscope is configured so that the first component includes elements such as the light source, which are rather expensive, while the second component, on the other hand, comprises elements that are relatively inexpensive. It is therefore possible to decouple the endoscope, and in this way inexpensive elements can be accommodated in a comparatively cost-effective single-use assembly, for example, whereas the less cost-effective expensive elements are accommodated in a multi-use assembly.

This now makes it possible for the first time to provide an endoscope that combines the advantages of very high-quality lighting with the advantages of an endoscope that is only intended for single use, for example. It should be noted that the endoscope according to the present disclosure does not necessarily have to be designed as a single-use endoscope or at least partially as a single-use endoscope. Rather, it is also conceivable to adapt this according to requirements.

However, it can be advantageous if the first component and the second component are coupled to one another so as to be detachable from one another. If the endoscope is designed as an endoscope that is at least partially intended for single use, the second component can be disposed of after use, for example. However, it is also possible that the second component is detachably coupled to the first component, while nevertheless being intended for multiple use and, after having been separated from the first component, is subjected to particular cleaning and sterilization processes designated for medical use.

The endoscope according to the present disclosure, which can also be described as a modular endoscope, therefore also offers the possibility of simplified manipulation on the one hand. On the other hand, high-quality lighting can be combined with the advantages of a single-use device, such as lighting by a laser, which provides for high light intensity, or a high power or high performance LED as light source, especially if the endoscope is a disposable endoscope or an endoscope at least partially designed as a disposable endoscope, i.e. an endoscope comprising at least some components that are intended for single use only.

The second component that includes a light guide may be rigid, for example, or else may be flexible. More generally, the second component can be understood as what is known as an endoscope shaft, and in the context of the present disclosure "shaft" is generally understood to mean both a rigid second component and a flexible component which, for example, merely comprises a flexible outer sheathing tube made of a polymer material, for example. If the second component is rigid, it may be designed such that, for example, the light guide forming part of the second component is at least partially surrounded by a tube section or by several tube sections made of a metal or a plastic. The exact design of the second component can be selected depending on the preferred field of application of the endoscope.

Light guides suitable for such endoscope systems may, for example, comprise some tens, some hundreds up to a few thousands of individual fibers, and the exact number of individual fibers included in the light guide depends on the addressed end diameter of the light guide and/or on the diameter of the individual fibers making up the light guide, for example. Usual fiber diameters range between 20 µm and 100 µm. Typical diameters are 30 µm, 50 µm, and 70 µm.

In particular for single-use endoscopes or for endoscope systems with small dimensions it may be advantageous to use a few thick fibers as the optical fibers in order to ensure sufficient luminance or illumination intensity in the area to be examined. On the one hand, this allows for cost-effective rapid assembly and, on the other hand, it ensures a high luminous flux emanating from the laser light source toward the distal end of the endoscope.

A number of not more than twenty of such individual fibers, preferably not more than ten of such individual fibers has been found to be advantageous and a good tradeoff between assembly cost and sufficient luminous flux transmission, although a single fiber may already be sufficient for extremely thin endoscope systems. Bundles made up of three or seven individual fibers offer the advantage that they can be packed very tightly in a common sheathing. The 7-fiber assembly has the particular advantage that a rather circular arrangement of the individual fibers can be achieved in the common sheathing and that a packing density ideal for fibers of circular cross section is resulting. With such a 7-fiber assembly it is then possible, for example, to distribute the individual fibers around the camera chip or around the image conductor at the distal end of the endoscope in such a way that uniform illumination of the tissue to be examined can be achieved. However, given the quite common square shape of laser chips or light emitting diode chips or of the converter as the light source, it may also be advantageous to use four individual fibers or integer multiples of four or of such fibers. On the one hand, with regard to the highest possible active fiber area, i.e. the actual light-conducting cross-sectional area of the fiber, the cavities available for lighting purposes can be filled with more fibers, and on the other hand, better light injection can be achieved.

It has been found to be advantageous for the one optical fiber or the plurality of optical fibers to have a diameter ranging from 100 μm to 1000 μm, preferably up to 500 μm, more preferably ranging from 150 μm to 400 μm. Fibers of this type are much more easily assembled as individual fibers and still have a sufficiently small minimum bending radius. For today's endoscopes with a camera chip of 1×1 mm², for example, four individual fibers, one at each side of the camera, with a diameter ranging from 200 μm to 300 μm would be ideal. Arrangements with a total of eight or twelve individual fibers, i.e. two or three fibers on each side of the camera, are preferred as well, and in this case the individual fibers will have a diameter ranging from 150 μm to 200 μm at most. It may also be suggested, for example, to use fibers with different diameters in order to allow the cavity between the camera chip and the surrounding sheathing to be filled in the closest possible way so that the highest possible luminous flux can be achieved. With a 12-fiber arrangement, i.e. three fibers on each camera side, the fiber in the middle could for instance have a diameter of about 250 μm, while the other two fibers only have a diameter between 100 μm and 150 μm.

Instead of the individual fibers, it is in principle also possible to use thin fiber bundles which in particular consist of very thin individual fibers with an individual fiber diameter of preferably less than 70 μm, most preferably less than 50 μm and which only have an extremely thin jacket that holds the fiber bundle together. Such fiber bundle designs are described in a not yet published parallel application of the present Applicant.

According to a further embodiment, the one optical fiber or the plurality of optical fibers are step-index glass fibers. Preferably, the one or more optical fibers are step-index glass fibers made of a glass composition that is free of lead and/or other heavy metals and free of antimony and/or arsenic and/or other critical elements such as Cr(VI), except for unavoidable traces.

In the context of the present disclosure, a fiber is understood to mean a body having a largest lateral dimension in one spatial direction of a Cartesian coordinate system that is larger than in the other two spatial directions perpendicular to this first spatial direction by at least a factor of 10, preferably by at least a factor of 50. In other words, a fiber is a very long, thin body.

In the context of the present disclosure, a step-index glass fiber is understood to mean a glass fiber having a refractive index that changes from the center, i.e. the core, outwards, in the form of at least one step. The glass fiber comprises a core glass and a cladding glass, the core glass having a different refractive index than the cladding glass.

A glass optical fiber comprises glass. Besides the glassy material, the glass optical fiber may furthermore comprise a further material at least partially enclosing the surface of the glassy material, which is known as surface sizing. Depending on the intended use, different glassy materials can be used for a glass optical fiber. In particular, the glass fiber may comprise a one-component and/or a multi-component glass. For example, the glass optical fiber may comprise fused silica as a substantially one-component glass and/or may in particular be in the form of a fused silica optical fiber, and the fused silica may also be doped, for example doped with OH ions and/or doped with fluorine, and/or may be provided in the form of water-rich or water-poor fused silica variations, for example, which will still be referred to as a one-component glass, or may comprise a multi-component glass, for example a multi-component silicate glass. Furthermore, the glass may also be in the form of a chalcogenide glass. Fused silica optical fiber or fused silica fiber also refers to a fiber comprising doped fused silica.

The optical fiber preferably comprises a fiber core and a fiber perimeter or fiber cladding layer. In preferred embodiments, the core, or core layer, respectively, is made of a core glass.

The optical fiber preferably comprises a fiber cladding surrounding the fiber core. In preferred embodiments, the fiber cladding comprises a cladding glass.

The fiber cladding preferably has a content of halogens or halides of less than 500 ppm (m/m), more preferably less than 400 ppm (m/m), yet more preferably less than 300 ppm (m/m), yet more preferably less than 250 ppm (m/m), yet more preferably less than 200 ppm (m/m), yet more preferably less than 150 ppm (m/m), yet more preferably less than 100 ppm (m/m), yet more preferably less than 80 ppm (m/m), yet more preferably less than 60 ppm (m/m), yet more preferably less than 40 ppm (m/m), yet more preferably less than 20 ppm (m/m), most preferably less than 10 ppm (m/m). In particularly preferred embodiments, the fiber cladding is free of halogens. Halogens include chlorine, fluorine, bromine, and/or iodine, or their anions, for example. An excessive concentration of halogens in the fiber cladding will lead to a formation of the corresponding halogen acids, in particular during steam sterilization, for example. Such halogen acids may reduce the resistance of the optical fiber article and may also be released therefrom. The halogen acids in particular attack materials such as stainless steel of autoclaves and endoscopes and cause the formation of undesirable rust.

The fiber core preferably has a content of halogens or halides of less than 500 ppm (m/m), more preferably less than 400 ppm (m/m), yet more preferably less than 300 ppm (m/m), yet more preferably less than 250 ppm (m/m), yet more preferably less than 200 ppm (m/m), yet more preferably less than 150 ppm (m/m), yet more preferably less than 100 ppm (m/m), yet more preferably less than 80 ppm (m/m), yet more preferably less than 60 ppm (m/m), yet more preferably less than 40 ppm (m/m), yet more preferably less than 20 ppm (m/m), most preferably less than 10 ppm (m/m). In particularly preferred embodiments, the core layer or the core is free of halogens. Halogens according to the invention include chlorine, fluorine, bromine, and/or iodine, or their anions, for example. An excessive concentration of halogens in the fiber core will lead to a formation of the corresponding halogen acids, in particular during steam sterilization, for example. Such halogen acids may reduce the resistance of the optical fiber article and may also be released therefrom. The halogen acids in particular attack materials such as stainless steel of autoclaves and endoscopes and cause the formation of undesirable rust.

In particular embodiments, the optical fiber is a fused silica fiber. In a particular embodiment, the fiber cladding and/or the fiber core includes a fraction of fused silica of at least 76 wt %, more preferably of at least 81 wt %, yet more preferably of at least 84 wt %, yet more preferably of at least 88 wt %, yet more preferably of at least 92 wt %, yet more preferably of at least 95 wt %, yet more preferably of at least 97 wt %, most preferably of at least 98 wt %. The higher the fraction of fused silica the better is chemical resistance and temperature resistance. Fused silica fibers may also be called quartz fibers or quartz glass fibers.

In one particular embodiment, the core glass has the following features:

The core glass preferably comprises at least 8 wt %, more preferably at least 23 wt %, yet more preferably at least 24 wt %, and most preferably at least 25 wt % or even at least 26 wt % of $SiO_2$. In a particular embodiment, the core glass may even comprise at least 28.3 wt % of $SiO_2$, most preferably at least 34 wt % of $SiO_2$. In some preferred embodiments, the core glass even comprises at least 35 wt % of $SiO_2$, more preferably at least 42 wt %.

Preferred core glasses of the present invention comprise the constituents in the composition ranges as listed below, in percent by weight:

| Component | from | to |
|---|---|---|
| $B_2O_3$ | 0 | 24 |
| $SiO_2$ | 23 | 62.1 |
| $Al_2O_3$ | 0 | 10 |
| $Li_2O$ | 0 | 10 |
| $Na_2O$ | 0 | 18.5 |
| $K_2O$ | 0 | 25.7 |
| BaO | 0 | 57.8 |
| ZnO | 0 | 40 |
| $La_2O_3$ | 0 | 25 |
| $ZrO_2$ | 0 | 10 |
| $HfO_2$ | 0 | 14.2 |
| $SnO_2$ | >0 | 2 |
| MgO | 0 | 8 |
| CaO | 0 | 8 |
| SrO | 0 | 24.4 |
| $Ta_2O_5$ | 0 | 22 |
| $Y_2O_3$ | 0 | 11.9 |
| $Rb_2O$ | 0 | 15 |
| $Cs_2O$ | 0 | 21 |
| $GeO_2$ | 0 | 7.5 |
| F | 0 | 2 |
| $\Sigma\ R_2O$ | 5 | 20 |
| $\Sigma$ MgO, CaO, SrO, ZnO | 20 | 42 |

$R_2O$ is the total of the respective contents of all alkali metal oxides.

One or more of the following components may be contained in the core glass: $Cs_2O$, $Rb_2O$, MgO, CaO, SrO, $Gd_2O_3$, $Lu_2O_3$, $Sc_2O_3$, $Y_2O_3$, $In_2O_3$, $Ga_2O_3$, and $WO_3$.

The following components should preferably not be contained in the core glass or only in concentrations of not more than 500 ppm each, such as caused by unavoidable impurities in the raw materials: $TiO_2$, $CeO_2$, $Nb_2O_5$, $MoO_3$, $Bi_2O_3$, PbO, CdO, $Tl_2O$, $As_2O_3$, $Sb_2O_3$, $SO_3$, $SeO_2$, $TeO_2$, BeO, radioactive elements and coloring components, unless otherwise described in the text. In particular $TiO_2$ should be avoided, since this component may lead to pronounced absorption in the UV range. In preferred embodiments, $WO_3$ is also dispensed with as a constituent.

The components $TiO_2$, $CeO_2$, $Nb_2O_5$, and/or $Bi_2O_3$ may be contained in the core glass in an amount of up to a maximum of 0.5 wt %, preferably up to 0.3 wt %, and most preferably up to 0.2 wt %. In a preferred embodiment, the core glass is free of these components.

The core glass is preferably free of optically active components, in particular $Sm_2O_3$, $Nd_2O_3$, $Dy_2O_3$, $Pr_2O_3$, $Eu_2O_3$, $Yb_2O_3$, $Tb_2O_3$, $Er_2O_3$, $Tm_2O_3$, and/or $Ho_2O_3$. $CeO_2$ absorbs in the UV range, so that preferred core glasses do not contain any $CeO_2$.

The total content of alkaline earth metal oxide components $La_2O_3$, $Ta_2O_5$, $ZrO_2$, and $HfO_2$ is preferably at least 40 wt %, more preferably at least 42 wt %, yet more preferably at least 50 wt %, and most preferably at least 55 wt %, especially for core glasses with refractive indices of greater than 1.65 wt %. If the content of these components is too low, the preferred refractive index can commonly not be obtained. Depending on the formulation, this total amount should not exceed a value of 72 wt %.

In one specific embodiment, the cladding glass has the following features:

The cladding glass preferably has an $SiO_2$ content of >60 wt %, more preferably >65 wt %, and most preferably at least 69 wt %. The $SiO_2$ content is preferably not more than 75 wt % and most preferably not more than 73 wt %. The cladding glass tends to be exposed to stronger environmental impacts than the core glass. A high $SiO_2$ content imparts better chemical resistance. Consequently, the content of this component in the cladding glass is preferably greater than in the core glass.

The composition of the cladding glass is preferably selected or adapted to that of the core glass in such a way that the coefficient of linear thermal expansion of the cladding glass and that of the core glass differ as little as possible. Commonly, the coefficient of thermal expansion (CTE) in a temperature range from 20 to 300° C. may be the same or may be different for the fiber core and the fiber cladding. In particular, the CTE is different. Preferably, the CTE of the cladding is lower than the CTE of the fiber core, typically it is lower by at least $1.0*10^{-6}$/K, but depending on the glass it may typically also be lower by at least $2.5*10^{-6}$/K. The fiber core typically has a CTE from $6.5*10^{-6}$ to $10*10^{-6}$/K, the cladding has a CTE from $4.5*10^{-6}$ to $6*10^{-6}$/K. This ensures that the core of the fiber shrinks more than the fiber cladding upon cooling, so that a compressive stress is built up in the fiber cladding, which protects the fiber, which is beneficial for the mechanical strength of the fiber, in particular its flexural strength.

The table below shows some preferred compositions of cladding glasses that can be used in combination with the core glasses. The cladding glasses comprise (in wt % on an oxide basis):

| Oxide | Group 1 | Group 2 | Group 3 | Group 4 |
|---|---|---|---|---|
| $SiO_2$ | 70-78 | 63-75 | 75-85 | 62-70 |
| $Al_2O_3$ | 5-10 | 1-7 | 1-5 | 1-10 |
| $B_2O_3$ | 5-14 | 0-3 | 10-14 | >15 |
| $Li_2O$ | none | 0-1 | 0-3 | <0.1 |
| $Na_2O$ | 0-10 | 8-20 | 2-8 | 0-10 |
| $K_2O$ | 0-10 | 0-6 | 0-1 | 0-10 |
| MgO | 0-1 | 0-5 | none | 0-5 |
| CaO | 0-2 | 1-9 | none | 0-5 |
| SrO | 0-1 | none | none | 0-5 |
| BaO | 0-1 | 0-5 | none | 0-5 |
| Halogen | none | none | none | none |

In another specific embodiment, the core glass and/or the cladding glass is a chalcogenide glass, which in particular allows applications in the infrared range. The table below shows preferred compositions of chalcogenide core glasses and/or chalcogenide cladding glasses, in mol percent:

| Component | Mol % |
|---|---|
| S | 50-90 |
| Ga | 0-25 |

-continued

| Component | Mol % |
|-----------|-------|
| As | 0-40 |
| Ge | 0-35 |
| $R^1$ (added in the form of $R^1$Hal) | 0-7.25 |
| $R^2$ (added in the form of $R^2$Hal) | 0-13.5 |
| $M^1$ (added in the form of $M^1$Hal$_2$) | 0-5 |
| $M^2$ (added in the form of $M^2$Hal$_2$) | 0-7.25 |
| Ln (added in the form of LnHal$_3$) | 0-4 |
| Total of Ga, As, and Ge | 10-42 |
| Total of $R^1$, $R^2$, $M^1$, $M^2$, and Ln | 0-16 |
| Total of halogens | 0-16 |

Here, Hal=fluorine, chlorine, bromine, and/or iodine; Hal$_2$ and/or Hal$_3$=chlorine and/or bromine; $R^1$=Li, Na, K, Rb, and/or Cs; $R^2$=Ag and/or Cu; $M^1$=Mg, Ca, Sr, and/or Ba; $M^2$=Zn, Cd, Hg, and/or Pb; Ln=La, Ce, Pr, Nd, Pm, Sm Eu, Gd, Tb, Dy, Ho, Er, Tm, Ty, Lu, Y, and Sc.

It is particularly advantageous if the glass fibers, fiber rods, or pressed fiber rods are made of a core glass and cladding glass that are free of Pb and heavy metals. Such fiber systems in particular offer high transmittance in the VIS spectral range and, due to their comparatively high transmittance in the blue spectral range, exhibit high color fidelity, which is particularly important for the medical assessment of tissue. Often only slight differences in color of the tissue decide whether this is a benign or malignant tissue change. It is therefore important to have a high CRI value for the overall system comprising the light source, light guide and imaging device, with CRI (Color Rendering Index) being a key figure of a photometric parameter that describes the quality of color rendering of light sources having the same correlated color temperature. With the glass fibers, fiber rods, or pressed fiber rods described above, a CRI value of >90 can be achieved. Such fiber systems are known from the present Applicant under the name SCHOTT PURAVIS® and have been described with regard to their composition in DE 102012100233 B4 and DE 102013208838 B4. Similar fiber systems which are likewise free of Pb are furthermore described in EP 2072477 B1.

In particular for use in endoscopes it is advantageous if glass fibers, fiber rods, or pressed fiber rods are made of a glass system which has an acceptance angle 2α of greater than 80°, most preferably greater than 100° for the light to be transmitted, which corresponds to a numerical aperture (NA) of greater than 0.64, most preferably greater than 0.77. What can be achieved thereby on the one hand is that in particular light from LEDs, which usually have a very wide emission angle, can be injected into the glass fibers or fiber rods or pressed fiber rods without elevated coupling losses, and this without the need for complex optics at the proximal end. On the other hand, wide-angle illumination can be achieved on the distal end without additional optics, which is most preferable for endoscopic examinations. Optimum illumination over the currently common camera viewing angles (usually 120° diagonally) can be achieved if the glass fibers, fiber rods, or pressed fiber rods have an acceptance angle 2α of at least 120° or an NA of at least 0.86.

Glass fibers as described above usually have a largely undamaged fire-polished surface after their drawing process, which must be protected in the best possible way from being damaged. For this purpose, a so-called sizing is applied to glass fibers prior to the winding process, which protects the fibers especially when the fibers rub against each other, but also when they come into contact with metal surfaces, for example. Such sizing usually consists of wax- or stearinbased solutions that are sprayed onto the glass fibers. Further types of sizing are described in a not yet published application of the present Applicant.

For further mechanical stabilization of the fiber, in particular in the case of fibers with a larger diameter as described above, it has been found to be advantageous if the one or more optical fibers have a polymer-based coating or a protective sheathing made of a polymer-based tube material arranged on their outer surface, at least on parts or sections thereof, for example in the form of a shrink tube. This allows to achieve higher strength and therefore also smaller bending radii of the fibers. The inherent drawback of a thicker fiber in terms of increasing rigidity and an increase in the minimum permissible bending radius can be significantly reduced or compensated for with this measure.

According to one embodiment, the light guide comprises a plurality of optical fibers, and at least one optical fiber, preferably a plurality of optical fibers, most preferably all optical fibers have a polymer-based coating and/or a protective sheathing made of a polymer-based flexible tube material arranged on their outer surface, at least partially and/or in sections thereof.

Preferable coatings include coatings made of a compound or several compounds selected from the group consisting of acrylates, polyamides, polyurethanes, polyimides, epoxy, ethylene-tetrafluoroethylene copolymers, and poly-xylene-based compounds (also referred to as poly-xylylene-based coatings), for example based on poly-para-xylene compounds, also known as a coating material under the trade name "Parylene", for example, or mixtures of these compounds.

Suitable coating materials are available, for example, under the trade names or brands or designations NYLON® (polyamide) or TEFZEL® or Parylene® or PMMA (polymethyl methacrylate) as coatings or coating materials. Such layers are usually cured by heating or by UV light. Alternatively or additionally, the coating may also comprise thermoplastic elastomers, for example a thermoplastic polyester elastomer or a thermoplastic copolyester elastomer as is commercially available under the trade name or trade mark Hytrel, for example, or a silicone.

In special cases, metallic coatings may also be used, for example made of gold or aluminum. Such conductive coatings may be advantageous, for instance, if it is necessary to shield electrical fields and/or to avoid electrical potentials, for example in cardiologic examinations of the heart, for which CF-classifications are necessary.

Particularly advantageously, such coatings are or can be applied to the one or more optical fibers by dip-coating, spray-coating, extrusion, or deposition at low pressure immediately after the fibers have been drawn. This in particular allows to achieve that the virtually perfect fire-polished surface of the fiber(s) is preserved before it comes into contact with other materials or with other fibers and before micro-damage can occur, that reduces the strength of the fiber(s). Protection against hydrolytic attack can also be achieved.

Such layers are usually applied by pulling the freshly drawn light guide in the form of a fiber through a pot with a nozzle, which holds the polymer material the coating is produced of, and the nozzle is also used to adjust the layer thickness, inter alia.

It is further possible, for example (see, for example, the Abstract of chapter "Fiber coating" by D. Hewak, Encyclopedia of Modern Optics") that the polymer material is configured to be hardened by UV-light, or that the coating is divided in an inner and an outer coating, wherein the inner coating may be softer (with lower Young's modulus) and the outer coating may be harder (with a higher Young's modulus), which may in particular be advantageous to minimize stress upon bending of such coated fibers. However, in principle, according to Hewak, other coatings comprising metal, ceramic or carbon as coating material, are possible.

Furthermore, an additional organic coating may be applied in addition to this first coating. Such additional coatings are also referred to as buffer coatings and are usually used for quartz fibers. Materials that may be considered for such buffer coatings include PMMA, polyamide (NYLON), polyimide, or one or several fluorinated polymer(s) such as an ethylene-tetrafluoroethylene copolymer (ETFE for short), which is commercially available under the trade name TEFZEL®, for example. Such a further coating serves to increase the robustness in terms of flexural strength. This buffer layer may in particular also comprise a thermoplastic elastomer, for example a thermoplastic polyester elastomer or a thermoplastic copolyester elastomer, such as commercially available under the trade name Hytrel®, for example, and/or polyvinylidene fluoride, for example available under the trade name Kynar, or polytetrafluoroethylene (e.g. available under the trade name Teflon), or polyurethane. Such buffer coatings may be applied by spray-coating, dip-coating, extrusion, and electrostatic techniques, for example.

Such a layer system may consist, for example, of a two-layer system in which a comparatively thin layer, typically 10 μm to 50 μm in thickness and made of an acrylate or epoxy compound, for example, is applied to the light guide, and then a so-called buffer layer, e.g. NYLON®, TEFZEL®, PMMA, or polyimide, is applied as a further mechanical protection, which will then have a significantly greater wall thickness of typically 50 μm up to 200 μm.

The layer thickness of this coating is typically in a range from 5 μm to 100 μm, preferably in the range from 10 μm to 50 μm. According to variants, a layer thickness of up to 200 μm may be provided for.

For applications with very little space, the first coating will be sufficient to ensure a flexural strength as high as possible.

It should be noted here that other methods are also conceivable, in particular to increase the strength of the fiber. For example, selective heat treatment processes similar to the thermal toughening of glass could be employed to produce a higher compressive stress close to the surface, which can increase the flexural strength of the fiber. Chemical toughening of the fiber is also conceivable. However, in order to maintain the optical properties of the fiber, an additional jacket would be necessary, so that a selective additional compressive stress can be produced in this additional jacket by ion exchange in a molten salt or by spray-coating a salt layer with subsequent heat treatment. Electron beam or ion beam toughening is also conceivable. However, all of these processes are comparatively complex. Moreover, it is difficult to retain the optical properties of the fibers.

According to a further embodiment, the coating may also be designed to be light-blocking, i.e. opaque, or light-absorbing, e.g. colored, such as black or blue. This is advantageous because it allows to reduce crosstalk to the camera chip.

An embodiment in which the light guide comprises at least one glass fiber, in particular a glass fiber comprising a multi-component silicate glass or a glass fiber made of a multi-component silicate glass, or preferably a glass fiber bundle which in particular is in the form of a glass fiber bundle comprising glass fibers comprising a multicomponent silicate glass or made of a multicomponent silicate glass or consisting of glass fibers made of a multicomponent silicate glass is particularly advantageous. This is because the optical properties of the glass fiber bundle and therefore of the light guide or of the diagnostic, surgical, and/or therapeutic device can be adapted particularly flexibly with such glass fibers. Furthermore, such light guides which are based on glass optical fibers, exhibit significantly higher temperature resistance than a polymer optical fiber (POF). This is in particular relevant if particularly good coupling efficiency is sought to be achieved and, for example, a thin fiber bundle made of or comprising glass optical fibers is directly contacted on an LED chip or arranged very close to such a chip. However, a polymer optical fiber or a fiber bundle composed of or comprising polymer optical fibers would not withstand such a thermal load, rather the fibers would melt.

According to one embodiment, the one optical fiber or the plurality of optical fibers are enclosed in an injection ferrule at the proximal end, which is designed as a mechanical interface to the laser light source and thus allows for a defined injection of light in terms of focus distance and centering relative to the light source. In the case of a single fiber or a plurality of individual fibers, ideally three or seven individual fibers, the injection ferrules may be provided in the form of so-called SMA connectors which in particular allow for defined alignment with the laser light source and are in particular also used for laser applications. So-called FC connectors are also conceivable for this purpose. Here, again, an arrangement of seven individual fibers is particularly advantageous, since this allows for a substantially circular cross-section on the one hand, and on the other for a minimized gusset area between the individual fibers. This has advantages in terms of coupling efficiency. Gusset refers to the interspaces in between a bundle of circular fibers. A further optimal fiber arrangement would result with 19 individual fibers, in which case the individual fibers are then optimally tightly packed in two shells around a central fiber. The individual fibers are usually fixed in place by an adhesive, e.g. a two-component hot-curing epoxy adhesive, or a UV-curing adhesive.

With respect to the rather common square or rectangular form of light-emitting diode or laser chips or a converter of a light source used as light source it can be advantageous to use four single fibers or integer multiples of four or two of such fibers so that the chip face is covered as good as possible. In this way, in the one hand the cavities present may be filled with respect to providing the highest possible active fiber area, that is, the actual-light conducting cross-sectional area of the fiber, with more fibers, and on the other hand, a better light coupling may be achieved.

In order to increase coupling efficiency, provision may also be made for the optical fibers to be provided in a hot-fused fashion at the proximal end. On the one hand, this allows to minimize gusset areas, since the hot deformation process deforms the per se round individual fibers so as to assume an at least approximately hexagonal cross-sectional shape, so they can be arranged almost without gaps. Moreover, more fibers can be accommodated for a given coupling cross-sectional area or focus diameter, so that a higher luminous flux can be transmitted.

It is possible for such hot-fused fibers to be accommodated in an injection ferrule at the proximal end, for example. However, it is also possible for the hot-fused fibers to be provided without a ferrule at the proximal end. This is particularly advantageous for embodiments which require efficient use of space, for example in the case of particularly small cross section areas at the proximal end, or the like.

According to a further embodiment, the at least one optical fiber and/or the plurality of optical fibers and/or the light guide is deformed at the distal end compared to the proximal end. This means that, according to one embodiment, the at least one optical fiber and/or the plurality of optical fibers and/or even the light guide itself may have a cross-sectional area with a shape that is different at the distal end from that at the proximal end. For example, it is possible that the cross-sectional area of the one fiber and/or of the plurality of fibers and/or of the light guide is substantially circular at the proximal end, i.e. within measurement accuracy, but is oval or kidney-shaped at the distal end, for example, or that the cross-sectional area at the distal end is delimited by at least two lines which have radii of curvature different from one another and/or which have the shape of a differential area of two only partially overlapping circles and/or ellipses. In particular, the cross-sectional area may have the shape of a circular segment, and for the case of a circular segment one of those radii of curvature is infinite, i.e. defining a straight line within measurement accuracy. Such a cross-sectional area in the form of a circular segment may also be referred to as a D-shaped cross-sectional area or a substantially D-shaped cross-sectional area.

It is also possible that different optical fibers have different cross-sectional shapes, more particularly the cross-sectional shape may be circular at the proximal end, but may be oval for one or more fibers and kidney-shaped for others at the distal end. Other cross-sectional shapes are also conceivable, for example rectangular or approximately rectangular cross-sectional shapes, in particular at the distal end, or, more generally, polygonal cross-sectional shapes. In particular, a cross section having the shape of a circular segment provides for excellent exploitation of the available cavities, here, and can thus result in an increased luminous flux or increased illuminance at the distal end of the endoscope.

Such a configuration may in particular be advantageous to ensure a particularly favorable spatial arrangement of the fiber and/or the fibers and/or of the light guide with respect to the camera chip.

More generally, it is possible for the at least one optical fiber and/or the optical fibers to have a cross-sectional shape different from a circular one, at least within measurement accuracy, at least in sections thereof. This may be advantageous in order to provide for particularly efficient, for example space-saving arrangements of individual elements in the second component of the endoscope.

This can be advantageous especially at the distal end of the light guide.

Therefore, according to one embodiment, the at least one optical fiber and/or the plurality of optical fibers has/have a flattened cross-sectional shape with an aspect ratio of at least 1.5:1 at least at the distal end of the light guide, and/or an oval cross section and/or a kidney-shaped cross-section, and/or a cross-sectional area that is delimited by at least two lines which have radii of curvature different from one another and/or which have the shape of a differential area of two only partially overlapping circles and/or ellipses.

As has been already mentioned further above, in particular assembling thin fiber bundles in a camera endoscope is very difficult and time consuming. Assembly can be realized more easily in particular with few thicker optical fibers. However, even in this case and further, without being restricted to the special embodiment of an endoscope requiring less assembly effort, in particular an endoscope comprising a light guide comprising few, comparatively thick single fibers, the problem arises that upon assembly of the camera and packaging of the fibers around the camera the fibers may be misaligned and the camera may be shifted to one side while being held in the middle of the distal housing for the camera and the fibers. This may result in the formation of unequal cavities voids so that an equal and defined distribution of fibers is no longer assured. This results in more fibers being arranged on one side of the camera than on another side of the camera, which may result to an unequal illumination of the tissue to be examined. A further disadvantage is that the optical fibers may emit light through the fiber mantle and that the camera may be sensitive to this scattered light at or on its side faces or may collect such scattered light. A poor image quality, for example, an insufficient contrast, or image artefacts may result. Conventionally, this problem may be solved by applying a light-blocking lacquer to the camera side walls or by molding an opaque epoxy resin in order to reduce uptake of scattered light, and/or by adhesively fixing the fibers and the camera within the housing or the shaft of the devices using a light-blocking adhesive. The usage of opaque adhesives, however, excludes the possibility of using UV- or light-curing adhesive for a rapid assembly. As the case may be, the relatively low temperature stability of camera chips may also exclude the usage of heat-curing adhesive. Therefore, typically adhesive with long curing times that can be cured at room temperature are used, which may result in a further dislocation of the camera position during curing. This may add to an offset position of the camera being located within the distal housing or the shaft. As a result, the optical fibers may further be arranged not in parallel, but at oblique angles or skewed with respect to each other, which may furthermore result in a negative influence on beam alignment. If fibers are ground and polished after assembly, oblique end faces may be obtained, for example, faces not at a right angle to the respective optical axis. Because of this, back-reflection may be higher and incidence of light on the target area may be lowered. This may also add to light being refracted not towards the targeted region or being inadvertently collected by the camera chip.

According to an aspect of the present disclosure, the present application therefore relates in general, to an endoscope comprising a light guide comprising at least one optical fiber, without being restricted to an endoscope with a light guide comprising at least one optical fiber with a diameter of at least 80 μm, that overcomes the aforementioned problems of the state of the art at least partially.

According to a variant, it may in general, without being restricted to an endoscope with simplified assembly due to the light guide being particularly formed, preferably so that the light guide comprises only few, but relatively thick single fibers with diameters of 80 μm or more, be provided that the endoscope comprises a housing or a housing element. The housing or housing element may provide an alignment for the optical fibers and comprise an accommodation for the camera chip in order to position it. Preferably, it may be provided to align and maintain the fibers in the desired locations and to position the camera chip in a defined manner centered within the housing or housing element. Preferably the housing or housing element may comprise one or more cut-out sections arranged at its outer surface for the defined accommodation, alignment and/or positioning of the one optical fiber or the several optical fibers. Particularly preferably, the cut-out sections have a cross section with preferably obliquely shaped side-walls, preferably a trapezoidal or tub-shaped cross section. In other words, according to an embodiment, the endoscope may comprise a housing or a further housing element that may, for example, already comprise the camera chip, the housing or housing element positioning the camera chip in a defined manner centered within the housing or housing element on the one hand and, on the other hand comprising one or more cut-out sections at its outer surface for the defined accommodation, alignment and/or positioning of the one optical fiber or the several optical fibers. The cut-out sections have a cross section with sidewalls, preferably a trapezoidal or tub-shaped cross section. According to an embodiment, the side-walls may draw an oblique angle. In another embodiment, the cut-out sections are not present and the housing may be formed from a single material that surrounds the optical fibers. The housing may extend along the length of the optical fibers in order to provide additional stability for the fibers. In this way, several of the aforementioned problems may be overcome at least partially and, at best, be minimized or be overcome even totally. For example, the optical axes of the optical fibers may be aligned in parallel to the camera upon assembly so that a skewed arrangement of the fibers may be reduced and oblique end faces during fiber grinding may be avoided. In particular, the preferably oblique side-walls of the for example trapezoidal or tub-shaped cut-out sections may enable a self-adjustment of the fiber position.

According to an embodiment, it may be contemplated to use an opaque or dark-colored, in particular a black colored, material for the housing. This is advantageous, as in this way a barrier for or shielding from stray light (or scattered light) between optical fibers and camera chip may be achieved. The aforementioned negative effects on image quality may be eliminated largely in this way. It is further advantageous using in particular a polymer material that may preferably be injection molded for the housing. In this way, complex geometries may be formed at comparatively low cost. Furthermore, in this way an additional electrical insulation may be achieved. Examples for suitable materials for such an embodiment are polycarbonate (PC), acrylonitrile butadiene styrene (ABS) and polyamide (PA).

In contrast to opaque or black colored adhesives used in conventional gluing of fibers, according to the aforementioned embodiments transparent, in particular UV-cure adhesives may be used, which may facilitate assembly sue to shorter curing times. A further advantage is that fibers may be positioned in such a way that they are offset to the rear with respect to the distal camera face. Here, the fibers may be broken or cut and may be potted with optically clear potting compound, such as an epoxy resin or a UV potting compound, without the need of grinding and polishing of the optical fibers and without impairing the objective of the camera chip. Further, in this way, a strain relief for sensitive wires or the flexible circuit may be achieved within the housing.

It may be noted here that these embodiments, for example a housing comprising cut-out sections for the optical fibers and/or further optical components, e.g. the mentioned cameras and/or optical elements for beam guiding or shaping or for integration of one or more light sources may be used both at the distal and the proximal end and, thus, in principal for other endoscopes, thereby giving rise to the aforementioned advantage, while the actual fiber diameter is of secondary importance only. In particular, it is thus according to this aspect possible and may even be contemplated that according to an embodiment a light guide comprising at least one optical fiber with a diameter between 30 μm and 70 μm is used. Further, according to an embodiment, the light guide may be formed as a fiber bundle comprising a multitude of thin optical fibers with diameters between 30 μm and 70 μm.

According to a further embodiment, the numerical aperture of the one or more optical fibers is at least 0.7, preferably at least 0.8, and most preferably at least 0.85. The core of the one or more optical fibers preferably comprises a glassy material with a composition that is selected from the glass compositions and glass composition ranges for core glasses listed above. In particular, the core of the glass fiber may predominantly comprise such a glassy material, that is to say at least 50 wt %, or essentially, i.e. at least 90 wt %, or even may completely be made thereof.

An embodiment in which the core of the one or more optical fibers comprises such a glassy material is advantageous because in this way it is possible to achieve very good illumination of the camera's field of view (here in particular for 1×1 mm² area CMOS cameras, for example).

According to a further embodiment, the one optical fiber or the plurality of optical fibers are designed such that the core and/or cladding glasses of the one optical fiber or of the plurality of optical fibers is free of lead and/or other heavy metals, and also free of antimony and/or arsenic and/or other critical elements such as Cr(VI), except for unavoidable traces.

According to an embodiment of the invention it may be provided for, as has been already described above, that the light source is formed as integrated component of the plug-in connector, that is, mounted within the plug-in connector, preferably integrally mounted. In that case it may be provided for that the former comprises a heat sink arranged within the plug-in connector, for example formed as a metal shaped part. Alternatively or additionally, an integrated LED driver circuit, that is, a driver circuit mounted within the plug-in connector, preferably an integrally mounted driver circuit may be provided, wherein the integrated LED or the integrated driver circuit may be connected to the first component via electrical contacts. Advantageously, in that case, the driver circuit may be formed as a space saving series resistor for the integrated LED that may further comprise, as voltage limitation, a supplementary protective diode, such as a Z-diode, byway of example. Alternatively, as integrated circuit, special constant current sources may be used that provide a fixed predetermined constant electric current for driving the integrated LED. It is particularly advantageous if a constant electric current is already fed from the first component of the endoscope to the integrated LED via the electrical contacts. In this way, the integrated LED driver circuit is no longer necessary so that plug-in connector installation space is saved. Further, in this way heat loss may be minimized in order to drive the integrated LED with as high electric current as possible without exceeding the maximum acceptable surface temperature for the plug-in connector.

In the scope of the present disclosure, a component is regarded as integrated if it is mounted within a further component, preferably integrally mounted. An integrated LED may therefore also be denoted a mounted LED. Accordingly, an integral component of a further component is a component mounted within the further component, preferably integrally mounted.

It has been proven to be quiet efficient for light coupling if light coupling between the integrated LED and the at least one optical fiber of the light guide is formed as butt joint, wherein the at least one optical fiber is bonded (or glued) directly to the chip of the integrated LED by means of a transparent adhesive glue. This is especially advantageous, as has been described above, when using a so-called wide-angle fiber with a high numerical aperture (NA) of at least 0.80. In this way, a great amount of the light emitted by the LED may be captured and guided to the distal end of the second component.

In most light diodes, the actual light emitting chip is protected by or molded within a layer in order to avoid direct contact with the environment, wherein the layer may be formed in a multitude of shapes. For example, the layer may be formed with an even surface or may form a convex or concave surface towards the chip, for example lens shaped or as spherical cap. Accordingly, bonding the optical fiber is also understood to refer to its fixing on or at said layer.

In a further aspect, the present invention relates to a disposable endoscope system comprising a first component and second components that are individually packaged in a sterile manner and which preferably are or can be in the form of shafts that, once removed from their sterile package, can be detachably coupled with the first component in order to obtain an endoscope, in particular an endoscope according to embodiments of the present disclosure.

In the context of the present disclosure, shaft refers to a second component of an endoscope, which has only a small cross-sectional area compared to its length. In other words, the shaft is thin compared to its length. Such a configuration of a second component in the form of a shaft is advantageous, especially when areas that are only very difficult to access are examined using the endoscope, and/or for applications in medical technology.

One advantage of the endoscope system according to the present disclosure is to have second components available, in particular shafts, that are already packaged in a sterile manner, for examinations in quick succession so that several areas can be examined quickly, or so that in the case of medical examinations several brief examinations of different patients can be carried out one after the other while ensuring adequate hygiene. Therefore, it is especially advantageous for the endoscope system according to the present disclosure that the second components can be coupled to the first component in a detachable manner in order to provide the advantages of a single-use endoscope, while at the same time the parts of the endoscope system which do not necessarily have to be sterilized in the case of medical examinations or for other medical purposes, for example, are accommodated in a first component that can be used repeatedly.

According to one embodiment, the second component is provided in the form of an at least partially flexible shaft which has a flexible sheathing comprising a flexible tube or braided tube or shrink tube, which encloses the light guide with its at least one optical fiber, at least in sections thereof, as well as a power supply line for electrically powering the camera chip and preferably at least one signal return line to a data and/or image processing unit that may in particular be provided as part of the first component. Such a configuration, in particular with a flexible shaft, is particularly suitable for medical applications.

According to a further embodiment, the second component is in the form of a shaft that is rigid at least in sections thereof, which has a rigid sheathing comprising a shell enclosing the light guide with its at least one optical fiber as well as a power supply line for electrically powering the camera chip and preferably at least one signal return line, preferably to a data and/or image processing unit that may in particular be provided as part of the first component. Such a configuration may be particularly advantageous since this allows to better protect the elements forming part of the second component, here in the form of a rigid shaft, against mechanical impacts.

BRIEF DESCRIPTION OF THE DRAWINGS

The invention will now be explained in more detail with reference to figures in which the same reference numerals designate the same or equivalent elements, and wherein:

FIGS. 3a to 3e are schematic views of distal ends of endoscopes, not drawn to scale, and FIGS. 4-6 show the distal end of an endoscope comprising a camera chip and a housing for said camera chip as a 3D-CAD model.

DETAILED DESCRIPTION

Figure 1:
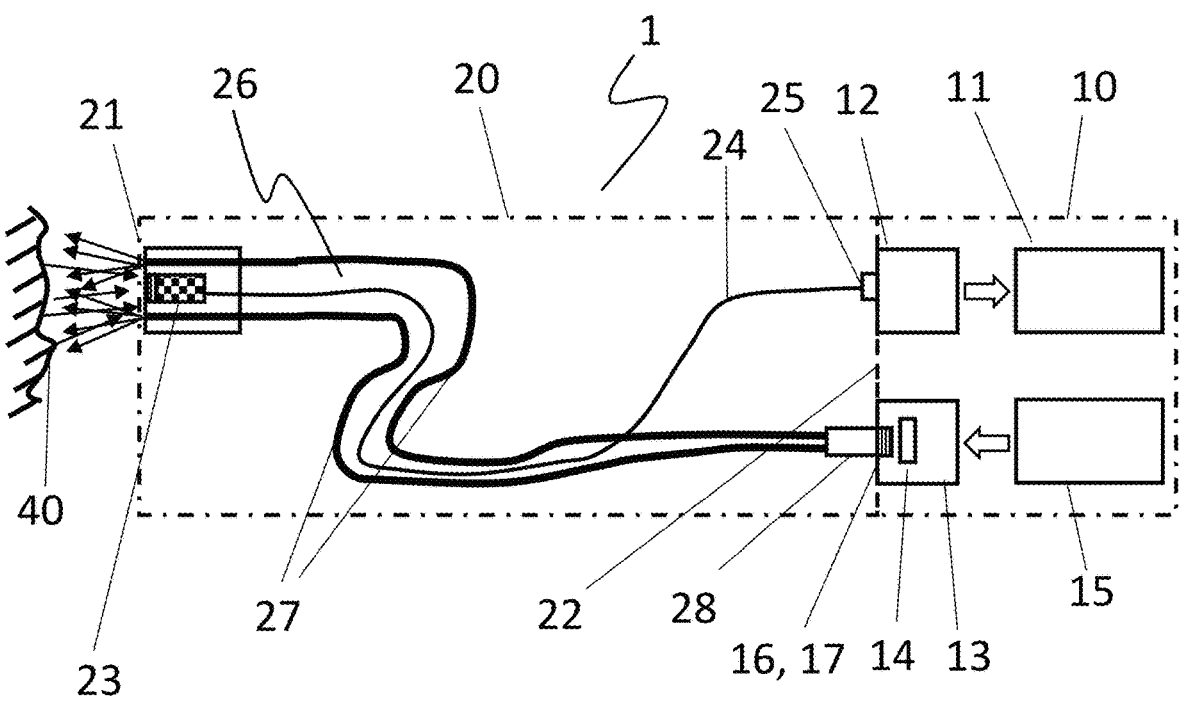
FIG. 1 shows a schematic view of an endoscope according to one embodiment, not drawn to scale.

FIG. 1 is a schematic view of an endoscope 1 according to one embodiment, not drawn to scale. Endoscope 1 comprises a first component 10 and a second component 20, with the first component 10 being shown on the right in the view, and the second component 20 on the left. The second component 20 has a proximal end 22 coupled to the first component 10. Provision may be made for the proximal end 22 of the second component 20 coupled to the first component 10 so as to be detachable. Thus, more particularly, the two components 20 and 10 may be provided in a form so as to be releasably coupled. This can be particularly advantageous if one component is only intended for single use, and if the other component, for example the first component 10 in the present case, comprises parts that are intended for multiple use, in particular high quality and/or expensive parts. This may in particular be the case if one of the components, here for example the first component 10, comprises a special light source such as a light source comprising at least one laser. This also applies to a data and/or image processing unit 11 as well as to a high quality light source 13 comprising high-power LED-chip 14 and its LED driver circuit 15 and power supply (not depicted) that may also be part of first component 10.

The second component 20 furthermore has a distal end 21 with a camera chip 23 disposed at the distal end 21, for capturing images of tissue surface 40. Furthermore, the second component 20 includes a light guide 26 extending therethrough and comprising at least one optical fiber 27, which is designed to conduct light of a light source 13 from the proximal end 22 to the distal end 21 of the light guide 26 and to emit it at the distal end 21 in order to illuminate tissue surface 40 as brightly and uniformly as possible. Furthermore, a power supply line (not shown) for electrically powering the camera chip 23 extends through the second component 20.

Light source 13 comprises at least one LED-chip 14 that is electrically powered by a driver circuit. Provision may be that at its optic interface 16, which is designed to accommodate an optical plug-in connector 28 of second component 20, an optical element, such as a lens or an array of lenses, is arranged, for injecting, for example, light emitted by LED-Chip 14 into the proximal end 22 of light guide 26 in optical fibers 27.

In particular under assembly considerations, especially if the second component 20 is only intended for single use, it may be advantageous if the light guide 26 comprises not more than at most twenty, preferably at most ten, optical fibers 27. However, more generally, it is also possible that a light guide 26 comprises up to a few hundred individual fibers 27, this being dependent on the respective fiber diameters and the resulting or addressed thickness of the fiber bundle and hence of the light guide 26, and the number of fibers 27 can be chosen accordingly.

Typical fiber diameters (or fiber thicknesses) of optical fibers 27 can preferably range from 100 µm to 1000 µm, more preferably up to 600 µm particularly preferably up to 500 µm, most preferably the maximum fiber diameter is in a range from 100 µm to 400 µm. However, thinner fibers with diameters of 30 µm, 50 µm or 70 µm are also conceivable.

According to one embodiment, the one optical fiber 27 or the plurality of optical fibers 27 is/are in the form of step-index glass fibers.

The one optical fiber 27 and/or the plurality of optical fibers 27 may preferably be designed such that the numerical aperture (NA) in air of the at least one fiber 27 and/or the plurality of optical fibers 27 is at least 0.7, preferably at least 0.8, and most preferably at least 0.85. This may be particularly beneficial for achieving a high CRI (Color Rendering Index) and in particular to achieve a high luminous flux at distal end 27.

In particular under assembly considerations it may be advantageous if the at least one optical fiber 27 or the plurality of optical fibers 27 are arranged in an optical plug-in connector, for example in the form of an injection ferrule at the proximal end 22 of light guide 26, as shown schematically in FIG. 1.

The second component 20 may be provided in the form of a shaft that is flexible at least in sections thereof, for example, or else as a shaft that is rigid at least in sections thereof. The second component may for instance comprise a sheathing. In the case where the second component 20 is provided in the form of a shaft that is flexible at least in sections thereof, the sheathing is designed to be flexible, in particular in the form of a flexible tube, braided tube, or shrink tube. In the case where the component 20 is provided in the form of a shaft that is rigid at least in sections thereof, the sheathing is preferably rigid and comprises a shell or a pipe section. More generally, without being limited to the example shown by way of example here, the sheathing encloses at least sections of the light guide 26 comprising the at least one fiber 27, and a power supply line for electrically powering the camera chip 23 and preferably at least one signal return line 24, preferably a line to a data and/or image processing unit 11 that may in particular be provided as part of the first component 10.

A particularly preferred exemplary embodiment has been found to be an assembly comprising seven optical fibers 27 of approximately 200 µm in thickness, which are designed as what is known as a wide-angle fiber with an NA>0.85, and the seven optical fibers 27 are arranged around the camera chip 23, and at the proximal end 22 they are glued into optical plug-in connector 28. Alternatively, these seven optical fibers 27 may also be hot-fused into optical plug-in connector 28. More generally, however, it is also possible and may even be preferred for hot-fused fibers to be provided without a ferrule at the proximal end.

Figure 2:
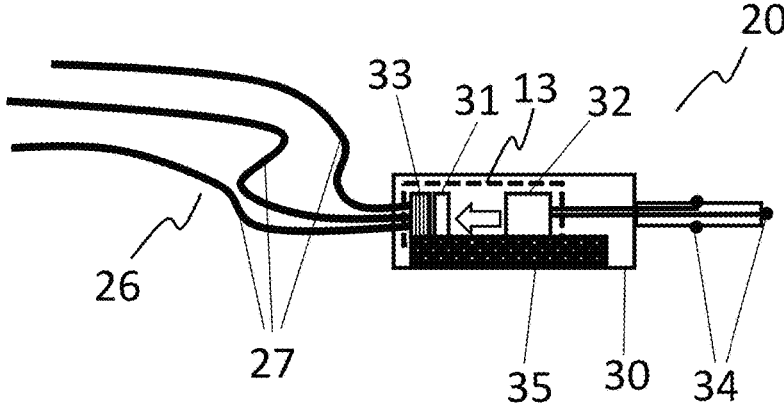
FIG. 2 shows a schematic section of an endoscope, not drawn to scale.

FIG. 2 also schematically shows a section of second component 20, in which the light source 13 is an integrated component of plug-in connector 30 forming proximal end of second component 22 with its light guide 26, and wherein the light source 13 comprises at least one integrated LED 31 injecting emitted light into the at least one optical fiber 27 of light guide 26.

The light source 13, formed as integrated component of plug-in connector 30, may additionally comprise a heat sink 35 and/or an integrated driver circuit 32, wherein the integrated LED 31 and/or the integrated driver circuit 32 may be coupled via electronic contacts 34 to the first component 10 of the endoscope.

It has been proven to be quiet efficient for light coupling if light coupling between the integrated LED 31 and the at least one optical fiber 27 of light guide 26 is formed as butt joint, wherein the at least one optical fiber 27 is bonded (or glued) directly to the front end side of the chip of integrated LED 31 by means of a transparent adhesive glue. Additionally it may be necessary that an optical element 33 in form of a simple lens or an array of lenses collimates the light so that as much light as possible can be injected into the fiber 27. Especially when using wide-angle fibers 27 with a high angle of acceptance (>100°) a direct butt joint often leads to better results, especially as Fresnel losses caused at junctions between further interfaces, here at the optical element 33, may be avoided.

It can, however, be advantageous if the optical element 33 is carried out as thin, transparent layer, for example as polymer film or as thin glass. In this way, in particular mechanical damages to the very thin converter layer of LED chjps of integrated the LED 31 are avoided. In particular, such a layer may be an effective mechanical protection for the embodiment shown in FIG. 1. Here, the optical element 17 could be carried out as polymer film or as thin glass. In particular in this embodiment, wherein the optical plug-in connector 28 of the second component 20 is often coupled to or decoupled from the optical interface 16, the LED chip 14 can be protected mechanically.

As LED chips in particular high-power compact white-light LED that may produce very high lumen values per watt a chip dimension of 1 mm² may be used either for the variant with the LED-chip being integrated in the first component of the endoscope or for the variant in which an integrated LED chip is integrated into the plug-in connector of the second component. In particular with such a comparatively small chip area a high coupling efficiency may be achieved. Examples of such LED are LUMILEDS LUXEON Z LXZ1-4080 that allows to achieve a CRI of 80 on the one hand and, on the other hand, a luminous flux of 130 m at 1.4 W for a chip dimension of 1 mm². A further example is OSRAM OSLON Pure 1010 which allows to achieve a CRI of 90 and generates a luminous flux of 95 lm.

With such LEDs it is possible to generate high enough lm-values, in particular for the variant with the LED integrated into the plug-in connector, even if these have to be driven in a controlled manner with respect to electricity and, thus, power in order not to exceed a maximum surface temperature at the plug-in connector.

FIGS. 3a to 3e show in schematically and not drawn to scale depictions of distal ends 21 of a second component 20 of an endoscope 1. In each case, the distal end 21 comprises the light guide 26 comprising here, in each case, several optical fibers 27 and a camera chip 23 in each case as well.

In FIG. 3a four fibers 27 are provided, each having a circular cross section within measurement accuracy. Here, these fibers are arranged around the camera chip 23 which has an approximately square shape in this case by way of example, and this in such a way that one fiber 27 is arranged on each respective side of the camera chip 23. In FIG. 3*d*, by contrast, fibers 27 are only arranged on three sides of the camera chip 23.

In FIG. 3*b*, only two fibers 27 are arranged on two sides of the camera chip 23. Here, the cross section of the optical fibers 27 is not circular, but rather oval or elliptical. The optical fibers 27 may in particular be formed so as to be deformed on the distal end 21 opposite to the proximal end 22—not shown here. It is in particular possible for the optical fibers 27 to have a circular cross section at the proximal end 22, but to be deformed at the distal end, as in the present example. This may be advantageous for arranging the fibers 27 around the camera chip 23.

The optical fibers 27 and/or the at least one optical fiber 27 may preferably have a flattened cross-sectional shape, at least at the distal end 21 as shown here byway of example, in particular with an aspect ratio of at least 1.5:1, and/or an oval cross-sectional shape, and/or a kidney-shaped cross sectional shape and/or a cross-sectional area that is delimited by at least two lines which have radii of curvature different from one another and/or which have the shape of a differential area of two only partially overlapping circles and/or ellipses. Although other cross-sectional shapes such as polygons are conceivable, flattened shapes are just particularly advantageous with regard to the arrangement of the optical fibers 27 around the camera chip 23. FIG. 3*c* shows an arrangement in which four fibers are arranged around the camera chip 23, which have a cross section having, here, the shape of a circular segment at their distal ends. Generally, without being restricted to the actual example of cross-sectional shapes shown here with cross sections having the shape of a circular segment and that may, by way of example, also be denoted as "D", cross sectional shapes are conceivable and advantageous that are delimited by at least two lines which have radii of curvature different from one another and/or which have the shape of a differential area of two only partially overlapping circles and/or ellipses. For example, generally, a crescent-shaped cross sectional shape is conceivable.

The distal ends of the fibers 27 shown in FIG. 3*b* as well as in FIG. 3*c* may be deformed in that way for example by a hot forming process. To this end, the fiber 27 is heated in a mold to above its working temperature and is then deformed under pressure. Due to the viscosity of the fiber material, it is of course impossible to reproduce perfect geometries. A cross section having the shape of a circular segment, that may also be described as D-shaped, will therefore have minor chamfers at the tapering corners. In principle, such a shaping process can be used for glass fibers, quartz fibers or else for plastic fibers, while the deformation temperature has to be adapted to the respective material. For plastic optical fibers (POFs) it will typically be between 150° C. and 300° C., for glass optical fibers typically between 500° C. and 800° C., depending on the type of glass, and for fused silica optical fibers up to 2000° C.

FIG. 3*e* shows a 12-fiber arrangement, as already described above. Here, a total of four thicker fibers 27 and eight thinner fibers are grouped in such a way that in each cavity (segment) the thick fiber 27 is arranged in the center of the cavity and the two thinner fibers 27 are arranged to the right and left of the thick fiber 27. Despite the fairly few fibers 27, the cavity space is very well exploited in this way, so that a comparatively high luminous flux can be achieved. Such examples may be expanded to a 20-fiber arrangement comprising 20 individual fibers 27, i.e. 5 fibers 27 in each cavity, ideally with 3 graduations in diameter for the fibers 27 in this case.

Figure 6:
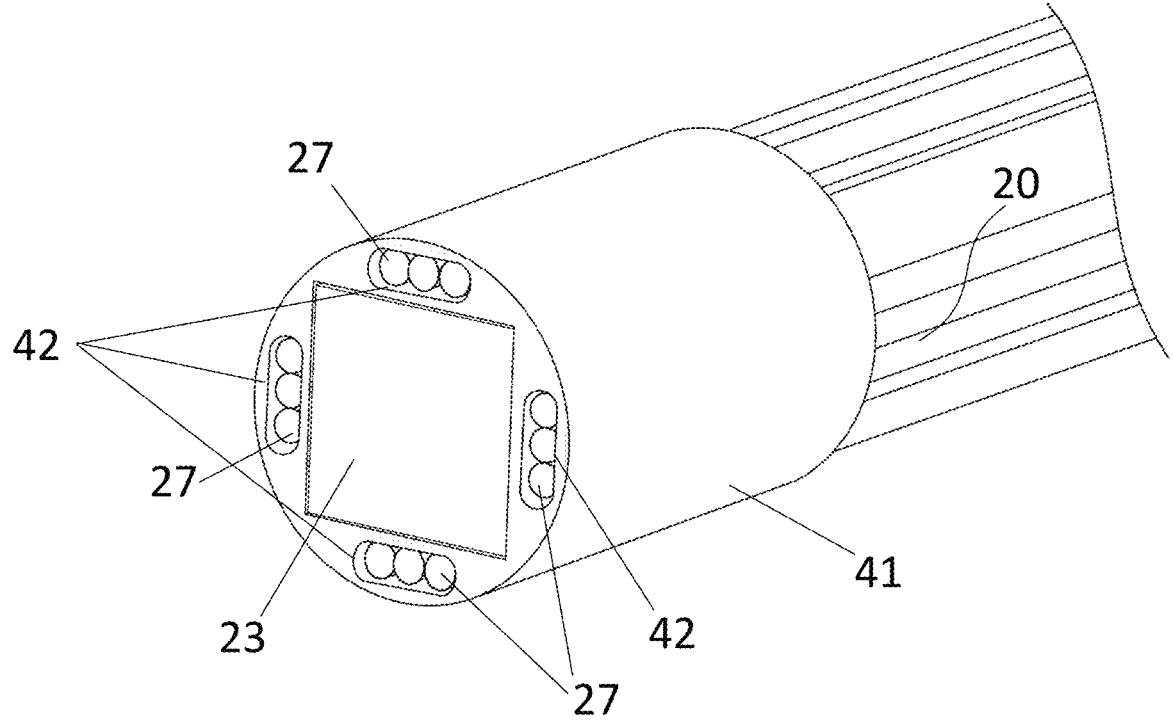

FIG. 4 depicts, as 3D-CAD model, distal end 21 of a second component of the endoscope 20 according to an embodiment with a twelve-fold arrangement of equally thick optical fibers 27 arranged around camera chip 23. According to an embodiment and without being restricted to the example depicted here, the endoscope includes housing 41 comprising an accommodation for camera chip 23 in order to fixedly position chip 23 and optical fibers 27. This housing 41 may for example be formed such that it comprises suitable cut-out sections 42 for optical fibers 27 in which optical fibers 27 may be arranged in a defined manner with respect to their orientation and angle. To this end, in FIG. 4, cut-out sections 42 are formed tub-shaped or trapezoidal. This is advantageous for an accordingly already largely parallel arrangement of fibers 27. Obliquely arranged and, therefore obliquely ground fibers 27 with the resulting disadvantages of light radiation at distal end 21 may be avoided with such an embodiment of housing 41 and cut-out sections 42. Further, assembly efforts may be reduced. Alternatively, the housing may for example be formed from a single material that surrounds the optical fibers a shown in FIG. 6.

FIG. 5 depicts a similar arrangement as depicted in FIG. 4, that is, mounted within a rigid shaft of a second component 20 of an endoscope. Further, in addition to the components describes with respect to FIG. 4 it can be seen that fibers 27 are guided largely parallel to each other in cut-out sections 42 of housing 41.

It may be noted here that housing 41 may be enclosed at least in parts or sections thereof by a rigid or flexible enclosure, for example in order to further promote fixing of optical fibers in cut-out sections 42 and to facilitate the further assembly even more. In particular when using few relatively thick fibers it is also conceivable to form housing 41 and the enclosure integrally so that the optical fibers may be inserted in thus formed, often slit-shaped sections or cut-outs.

With regard to shielding the camera chip 23 from lateral extraneous light coming from optical fibers 27, housing 41 may ideally be made of an opaque, light blocking material. Particularly suited are injection molded parts made of black colored plastic, for example made of or comprising polycarbonate (PC) or polyamide (PA). Further, for fixing the fibers, it is conceivable to use an opaque, for example, also a black colored, adhesive. However, housing 41 made of, for example, a black plastic material, allows for usage of transparent, for example, UV-cure adhesives, which results in a shorter manufacturing process and thus, cost advantage. Further, signal return line 24 has been depicted and denoted.

LIST OF REFERENCE NUMERALS

1 Endoscope
10 First component of endoscope
11 Data and/or image processing unit
13 Light source
14 LED chip
15 LED driver circuit
16 Optical interface
17 Optical element
20 Second component of endoscope
21 Distal end of second component
22 Proximal end of second component
23 Camera chip
24 Signal return line
25 Electrical plug-in connector
26 Light guide 27 Optical fiber(s)
28 Optical plug-in connector
30 Plug-in connector
31 Integrated LED
32 Integrated LED driver circuit
33 Optical element
34 Electrical contacts
35 Heat sink
40 Tissue surface
41 Housing
42 Cut-out section

What is claimed is:

1. An endoscope comprising:
a first component having a proximal end, a distal end, a light source comprising an LED chip that emits light, a data and/or image processing unit and an LED driver;
a second component having a proximal end, a distal end, an image capturing element, at least one signal return line to the data and/or image processing unit and a light guide, the proximal end being detachably coupled to the distal end of the first component, the image capturing element being arranged at the distal end, the light guide comprising an optical fiber extending through the second component, wherein the LED chip is coupled to the proximal end of the second component so that the light is injected into the optical fiber and is conducted from the LED chip at the proximal end of the second component to the distal end of the second component to emit the light at the distal end,
wherein the optical fiber has a cross section of at least 80 μm, and
wherein the optical fiber has a polymer-based coating, or a protective sheathing made of a polymer-based tube material arranged on an outer surface; and a housing disposed at the distal end of the second component, wherein the housing has a surface facing away from the distal end of the second component, the surface having a center, wherein the surface has cut-out sections to position the image capturing element in a desired location and to position the optical fiber at a location around the image capturing element, wherein the cut-out sections in the surface of the housing comprise a cut-out section at an outer surface, and wherein the cut-out section at the outer surface has obliquely shaped sidewalls.

2. The endoscope of claim 1, wherein the polymer-based coating or the protective sheathing is on parts or sections of the outer surface of the optical fiber.

3. The endoscope of claim 1, further comprising a plug-in connector formed at the proximal end of the second component, wherein the LED chip is positioned to inject light into the optical fiber formed as an integrated component of the plug-in connector.

4. The endoscope of claim 1, wherein the optical fiber comprises a plurality of optical fibers.

5. The endoscope of claim 4, wherein the plurality of optical fibers comprises not more than twenty optical fibers.

6. The endoscope of claim 4, wherein the plurality of optical fibers comprises not more than ten optical fibers.

7. The endoscope of claim 1, wherein the image capturing element comprises a camera chip.

8. The endoscope of claim 1, wherein the image capturing element comprises a camera chip and the endoscope further comprises a power supply line for electrically powering the camera chip.

9. The endoscope of claim 1, wherein the cross section of the optical fiber is up to 1000 μm.

10. The endoscope of claim 1, wherein the optical fiber is a step-index glass fiber comprising a glass composition that is free, except for unavoidable traces, of a material selected from a group consisting of lead, heavy metals, antimony, arsenic, critical elements, Cr(VI), and any combinations thereof.

11. The endoscope of claim 1, wherein the optical fiber has a numerical aperture (NA) in air of at least 0.7.

12. The endoscope of claim 1, wherein the polymer-based coating or the protective sheathing comprises a compound selected from a group consisting of acrylate, polyurethane, polyimide, epoxy, polyamide, ethylene, tetrafluoroethylene copolymer, poly-xylene-based compound, and any mixtures thereof.

13. The endoscope of claim 1, wherein the polymer-based coating or the protective sheathing is a coating selected from a group consisting of a dip-coating, a spray-coating, an extrusion coating, and a low-pressure deposition coating.

14. The endoscope of claim 1, wherein the polymer-based coating or the protective sheathing has a thickness between at least 5 μm and at most 100 μm.

15. The endoscope of claim 1, wherein the optical fiber is deformed at the distal end of the second component as compared to the optical fiber at the proximal end of the second component.

16. The endoscope of claim 1, wherein the LED chip is coupled to the proximal end of the second component in a butt joint.

17. The endoscope of claim 1, wherein the housing comprises a polymer material having a color selected from a group consisting of opaque colors, dark-colored, and black colored.

18. The endoscope of claim 1, wherein the first component and the second component are releasably connected.

19. The endoscope according to claim 1, wherein the surface of the housing only has cut-out sections to position the image capturing element in a desired location proximal the center of the surface of the housing, and to position the optical fiber at locations around the image capturing element.

20. The endoscope according to claim 1, wherein the cut-out section in the surface of the housing for the image capturing device positions the image capturing device proximal the center of the surface of the housing, wherein the optical fiber comprises a plurality of optical fibers, and wherein the plurality of optical fibers are located in cut-out sections in the housing in a position selected from the group consisting of inside the housing, on an outer surface of the housing, and a combination thereof.

21. An endoscope comprising:
a first component comprising a housing having a proximal end and a distal end, and containing a light source comprising an LED chip that emits light, an LED driver, and at least one of a data unit and an image processing unit; and
a second component comprising a housing having a proximal end and a distal end, and containing an image capturing element, at least one signal return line to the data and/or image processing unit and a light guide, the proximal end being detachably coupled to the distal end of the first component, the image capturing element being arranged at the distal end, the light guide comprising an optical fiber extending through the second component, wherein the LED chip is coupled to the proximal end of the second component so that the light is injected into the optical fiber and is conducted from the LED chip at the proximal end of the second component to the distal end of the second component to emit the light at the distal end, wherein a housing is disposed at the distal end of the second component, wherein the housing has a surface facing away from the distal end of the second component, and wherein the surface of the housing facing away from the distal end of the second component has cut-out sections to position the image capturing element in a desired location in the surface and to position the optical fiber at a location around the image capturing element, wherein the cut-out sections in the surface of the housing comprise a cut-out section at an outer surface, and wherein the cut-out section at the outer surface has obliquely shaped sidewalls.

22. The endoscope according to claim 21, wherein the cut-out section in the surface of the housing for the image capturing device positions the image capturing device proximal a center of the surface of the housing, wherein the optical fiber comprises a plurality of optical fibers, and wherein the plurality of optical fibers are located in a position selected from the group consisting of inside the housing, on an outer surface of the housing, and a combination thereof.

23. The endoscope according to claim 21, wherein the at least one optical fiber comprises a plurality of optical fibers and the cut-out sections in the housing for positioning the optical fibers are designed and configured to position the plurality of optical fibers around at least a portion of the image capturing device, and wherein the plurality of optical fibers is located on an outer surface of the housing.

24. The endoscope according to claim 21, wherein the surface of the housing only has cut-out sections to position the image capturing element in a desired location proximal a center of the surface of the housing, and to position the at least one optical fiber at locations around the image capturing element.

25. The endoscope according to claim 21, wherein the optical fiber is directly bonded to the housing.

26. The endoscope according to claim 25, wherein the optical fiber directly bonded to the housing using a transparent adhesive.

27. The endoscope according to claim 21, wherein the housing is formed from an opaque, light blocking material.

28. The endoscope according to claim 27, wherein the housing is formed from an injection molded polymer material.

29. The endoscope according to claim 28, wherein the polymer material is selected from the group consisting of polycarbonate (PC), acrylonitrile butadiene styrene (ABS), and polyamide (PA).

* * * * *